US010758645B2

(12) United States Patent
McNamara et al.

(10) Patent No.: US 10,758,645 B2
(45) Date of Patent: Sep. 1, 2020

(54) INJECTABLE, FLEXIBLE HYDROXYAPATITE-SILK FOAMS FOR OSTEOCHONDRAL AND DENTAL REPAIR

(71) Applicant: Tufts University, Medford, MA (US)

(72) Inventors: Stephanie L. McNamara, North Attleboro, MA (US); Benjamin P. Partlow, Winchester, MA (US); David L. Kaplan, Concord, MA (US)

(73) Assignee: Tufts University, Medford, MA (US)

( * ) Notice: Subject to any disclaimer, the term of this patent is extended or adjusted under 35 U.S.C. 154(b) by 339 days.

(21) Appl. No.: 15/536,261

(22) PCT Filed: Dec. 17, 2015

(86) PCT No.: PCT/US2015/066470
§ 371 (c)(1),
(2) Date: Jun. 15, 2017

(87) PCT Pub. No.: WO2016/100721
PCT Pub. Date: Jun. 23, 2016

(65) Prior Publication Data
US 2018/0243479 A1   Aug. 30, 2018

Related U.S. Application Data

(60) Provisional application No. 62/093,122, filed on Dec. 17, 2014.

(51) Int. Cl.
*A61L 27/46* (2006.01)
*A61L 27/38* (2006.01)
*A61L 27/22* (2006.01)
*A61L 27/56* (2006.01)
*C07K 14/435* (2006.01)

(52) U.S. Cl.
CPC ............ *A61L 27/46* (2013.01); *A61L 27/227* (2013.01); *A61L 27/3821* (2013.01); *A61L 27/56* (2013.01); *C07K 14/43586* (2013.01); *A61L 2400/06* (2013.01); *A61L 2430/02* (2013.01); *A61L 2430/12* (2013.01)

(58) Field of Classification Search
None
See application file for complete search history.

(56) References Cited

U.S. PATENT DOCUMENTS

| 4,806,355 A | 2/1989 | Goosen et al. |
| 5,015,476 A | 5/1991 | Cochrum et al. |
| 5,093,489 A | 3/1992 | Diamantoglou |
| 5,245,012 A | 9/1993 | Lombari et al. |
| 5,263,992 A | 11/1993 | Guire |
| 5,270,419 A | 12/1993 | Domb |
| 5,576,881 A | 11/1996 | Doerr et al. |
| 5,902,800 A | 5/1999 | Green et al. |
| 6,127,143 A | 10/2000 | Gunasekaran |
| 6,245,537 B1 | 6/2001 | Williams et al. |
| 6,267,776 B1 | 7/2001 | O'Connell |
| 6,302,848 B1 | 10/2001 | Larson et al. |
| 6,310,188 B1 | 10/2001 | Mukherjee |
| 6,325,810 B1 | 12/2001 | Hamilton et al. |
| 6,337,198 B1 | 1/2002 | Levene et al. |
| 6,372,244 B1 | 4/2002 | Antanavich et al. |
| 6,379,690 B2 | 4/2002 | Blanchard et al. |
| 6,387,413 B1 | 5/2002 | Miyata et al. |
| 6,395,734 B1 | 5/2002 | Tang et al. |

FOREIGN PATENT DOCUMENTS

| WO | WO-1997/008315 A1 | 3/1997 |
| WO | WO-2016/100721 A1 | 6/2016 |

OTHER PUBLICATIONS

Yan, L.-P. et al., Nanomedicine, 2013 vol. 8, No. 3, pp. 359-378.*
Altman, G. H. et al., Silk-based biomaterials, Biomaterials, 24: 401-416 (2003).
International Search Report for PCT/US2015/066470, 2 pages (dated Apr. 28, 2016).
Kikuchi, Y. et al, Structure of the *Bombyx mori* fibroin light-chain-encoding gene: upstream sequence elements common to the light and heavy chain, Gene, 110:151-158 (1992).
Kino, R. et al., Preparation and characterization of multilayered hydroxyapatite/silk fibroin film, J. Biosci. Bioeng., 103(6):514-20 (2007) [abstract].
Lucas, F. et al., The Silk Fibroins, Adv. Protein Chem, 13: 107-242 (1958).
Omenetto, F. G. and Kaplan, D. L., New Opportunities for an Ancient Material, Science 329: 528-531 (2010).
Partlow, B.P. et al., Highly tunable elastomeric silk biomaterials, Adv. Funct. Mater., 24(29):4615-4624 (2014).
Radev, L. et al., Silk Fibroin/Calcium Phosphate Silicate Composites: In vitro Bioactivity, International Journal of Materials and Chemistry, 3(3A):8-15 (2013).
Rockwood, D. N. et al, Materials fabrication from *Bombyx mori* silk fibroin, Nature Protocols, 6(10):1612-31 (2011).
Sashina, E. S. et al., Structure and Solubility of Natural Silk Fibroin, Russ. J. Appl. Chem, 79(6): 869-876 (2006).
Shen-Zhou, L. et al., Preparation and characterization of silk fibroin/hydroxyapatite porous composite materials, Journal of Clinical Rehabilitative Tissue Engineering Research, 13(34):6789-6792 (2009).
Takei, F. et al, Further Evidence for Importance of the Subunit Combination of Silk Fibroin in its Efficient Secretion from the Posterior Silk Gland Cells, J. Cell Biol., 105:175-180 (1987).

(Continued)

*Primary Examiner* — Heidi Reese
(74) *Attorney, Agent, or Firm* — Quarles & Brady, LLP

(57) ABSTRACT

The present invention provides, among other things, a silk ceramic material having enzymatically cross-linked amino acid side chains to generate injectable and flexible foam ceramics. Provided are compositions and methods of producing soft, flexible ceramic foam with silk polymeric crosslinking to serve as binders. Materials have applications in osteochondral and dental replacement and repair.

16 Claims, 12 Drawing Sheets

(56) References Cited

OTHER PUBLICATIONS

Tanaka, K. et al, Determination of the site of disulfide linkage between heavy and light chains of silk fibroin produced by *Bombyx mori*, Biochim. Biophys. Acta., 1432:92-103 (1999).

Tanaka, K., et al, Immunological Identification of the Major Disulfide-Linked Light Component of Silk Fibroin, J. Biochem. 114(1):1-4 (1993).

Vepari, C. and Kaplan, D. L., Silk as a biomaterial, Prog. Polym. Sci., 32: 991-1007 (2007).

Written Opinion for PCT/US2015/066470, 4 pages (dated Apr. 28, 2016).

\* cited by examiner

INJECTABLE, FLEXIBLE HYDROXYAPATITE-SILK FOAMS FOR OSTEOCHONDRAL AND DENTAL REPAIR

GOVERNMENT SUPPORT

This invention was made with government support under grant number EB002520 awarded by the National Institutes of Health. The government has certain rights in the invention.

BACKGROUND

Silk fibroins are produced by numerous species of spiders and by worms from various insects such as bees, butterflies, and moths. Silks produced by silkworms (typically *Bombyx mori*) and orb-weaving spiders have desirable mechanical properties, environmental stability, biocompatibility, and tunable degradation. In addition, these silks can be modified to deliver agents such as antibiotics, drugs, and growth factors to enhance healing in biomedical applications. Silk has been previously discussed in the context of biomedical applications, such as silk sutures (Vepari and Kaplan 2007).

SUMMARY

The present invention provides, among other things, new silk ceramic materials/compositions. As used herein, when referring to certain embodiments, the terms "composition" and "material" are used interchangeably. In some embodiments, provided compositions are or comprise flexible silk foams (e.g., flexible silk-ceramic foams). In some embodiments, silk fibroin may serve as a binder for one or more inorganic materials according to certain provided flexible compositions of the present invention, such as through one or more crosslinking reactions. According to various embodiments, provided foams are useful, for example, for osteochondral and dental applications including replacement and repair. The present invention also provides methods of preparing and using such provided foams.

In some embodiments, provided methods and compositions may be useful as a repair material for bone. In general, bone is a complex, hierarchical composite consisting of both inorganic and organic components. This includes about 40-50% calcium deficient ion-substituted hydroxyapatite in the form of elongated crystals, about 30-40% type I collagen fibers, and the remaining 10% of water and cellular components. Osseous tissue is highly vascularized, dynamic, and adapts to changes in mechanical loading. Bone exhibits anisotropic behavior in that its mechanical properties are directionally dependent, and it resists loading best in the axial direction. Human compact bone has a compressive strength of about 170-200 MPa, a tensile strength of about 100-120 MPa, and a shear strength of about 60-80 MPa. Although bone is rather brittle, it does exhibit a certain degree of elasticity conferred by the type I collagen fiber reinforcement. According to various embodiments, provided compositions allow for the repair of damaged or missing tissue.

In some embodiments, provided methods and compositions allow for the creation of silk-ceramic materials (e.g., foams) that were previously unattainable. In some embodiments, provided compositions comprise a proportion of solid content of between 10% to 80%. In some embodiments, at least 80% (e.g., 85%, 90%, 95%, 99%) of the solids in a provided composition are or comprise inorganic material. In some embodiments, provided compositions may comprise more than 90% inorganic material and less than 10% silk material (e.g., silk fibroin). Also in certain embodiments, provided compositions may be characterized as having a Young's modulus of at least 1 MPa (e.g., at least 1.5 MPa, 2 MPa, 2.5 MPa, 3 MPa, or 3.5 MPa).

In some embodiments, the present invention provides methods of producing a silk ceramic material including the steps of: subjecting a composition comprising silk fibroin and a calcium phosphate material to enzymatic crosslinking under conditions and for a period of time sufficient to convert the material from a first state that is substantially free of beta sheet character with no solid form structure to a second state having significant beta sheet character, the composition being characterized in that an otherwise comparable composition lacking the calcium phosphate and comparably exposed to enzymatic crosslinking under the conditions and for the period of time does not produce a material state with such beta sheet character and with such stiffness, toughness, and mechanical rigidity.

In some embodiments, silk fibroin is present in the composition at a weight percent within the range of about 0.1% to about 50%. (e.g., about 0.1% to 40%, 0.1% to 30%, 0.1% to 20%, 0.1% to 10%, 1% to 50%, 1% to 40%, 1% to 30%, 1% to 20%, 1% to 10%, etc) In some embodiments, calcium phosphate material is present in the composition at a weight percent within the range of about 30% to about 90% (e.g., about 30% to 80%, 30% to 70%, 30% to 60%, 30% to 50%, 30% to 40%, 40% to 90%, 50% to 90%, 60% to 90%, 70% to 90%, 80% to 90%). In some embodiments, calcium phosphate material and silk fibroin are present in relative weight percent amounts within a range of about 1:2 to about 4:5. In some embodiments, silk fibroin has a molecular weight within the range of about 10 kDa to about 450 kDa (e.g., about 10 kDa to 400 kDa, 10 kDa to 350 kDa, 10 kDa to 300 kDa, 10 kDa to 250 kDa, 10 kDa to 200 kDa, 10 kDa to 150 kDa, 10 kDa to 100 kDa, etc).

In some embodiments, a provided composition is or comprises a solution. In some embodiments, a provided composition is or comprises a paste. In some embodiments, a provided composition is or comprises a slurry.

In some embodiments, provided methods and compositions further comprise one or more crosslinking enzymes; and the step of subjecting comprises adding to the composition a substrate for the enzyme so that the enzyme introduces crosslinks into the composition. In some embodiments, crosslinks comprise crosslinks between silk fibroin amino acid residues. In some embodiments, crosslinks comprise crosslinks between silk fibroin tyrosine residues. In some embodiments, a crosslinking enzyme is selected from a peroxidase, a lignin peroxidase, laccase, tyrosinase, an oxidase, and an oxidoreductase. In some embodiments, crosslinking is introduced via one or more non-enzymatic means (e.g., dehydration, mechanical force, and/or thermodynamic treatments).

In some embodiments, the second state of provided materials is characterized by one or more of a compressive toughness of between 1-20 kJm$^3$ (e.g., 1-15 kJm$^3$, 1-10 kJm$^3$, 1-5 kJm$^3$, 2-20 kJm$^3$, 2-15 kJm$^3$, 2-10 kJm$^3$, 5-20 kJm$^3$, 5-15 kJm$^3$, 5-10 kJm$^3$, etc), inclusive, and a compressive elastic modulus between 1-5 MPa at 5% strain (e.g., 1-4 MPa, 1-3 MPa, 1-2 MPa), inclusive.

In some embodiments, provided methods further comprise a step of providing the composition by combining a solution comprising the silk fibroin, and a powder comprising the calcium phosphate material.

In some embodiments, the solution is prepared by a process that includes boiling for a period of time within the range of 1 minute and 120 minutes, inclusive. In some embodiments, the boiling is performed under conditions and for a period of time so that the silk fibroin has a molecular weight within the range of 3.5 kDa to 450 kDa (e.g., 5 kDa to 450 kDa, 10 kDa to 450 kDa, 10 kDa to 400 kDa, 10 kDa to 300 kDa, 10 kDa to 200 kDa, 10 kDa to 100 kDa). In some embodiments, the boiling is performed under conditions and for a period of time so that the silk fibroin has a molecular weight within the range of 300 kDa to 450 kDa. In some embodiments, the boiling is performed under conditions and for a period of time so that the silk fibroin has a molecular weight within the range of 3.5 kDa to 300 kDa.

In some embodiments, the step of providing the composition comprises combining the powder and the solution in a relative proportion within a range of 0.5 to 0.8 (e.g., 0.5 to 0.75, 0.5 to 0.7, 0.5 to 0.65, 0.5 to 0.6, 0.5 to 0.55, 0.6 to 0.8, 0.7 to 0.8, etc). In some embodiments, the step of providing the composition comprises combining the powder and the solution in a relative proportion within a range of 0.6 to 0.7.

In some embodiments, the present invention provides methods including the step of administering to a site in a body a composition comprising: a calcium phosphate and crosslinked silk fibroin, so that the composition comprises at least 80% organic material, which composition is characterized in that, within a period of time after the administering, the material transitions from a first state characterized by substantially no beta sheet content to a second state characterized by substantial beta sheet content. In some embodiments, the step of administering further comprises combining a solution comprising the silk fibroin, a powder comprising the calcium phosphate material, and an oxidative enzyme with hydrogen peroxide during administration of the composition. In some embodiments, the step of administering further comprises combining a solution comprising the silk fibroin, a powder comprising the calcium phosphate material, and an oxidative enzyme with a substrate (e.g., hydrogen peroxide) after administration.

In some embodiments, silk ceramic materials are provided. In some embodiments, the present invention provides silk ceramic material suitable for use as, inter alia, an implant for the repair, augmentation, and/or replacement of at least a part of one or more bones. In some embodiments, the present invention provides silk ceramic materials for use as, inter alia, an implant for the repair, augmentation, and/or replacement of substantially all of one or more bones. In some embodiments, the present invention provides silk ceramic material for use as, inter alia, an implant a supplement to, or substitute for, one or more bone grafts.

In some embodiments, provided silk ceramic materials (e.g., foams) comprise crosslinked protein (e.g., silk) polymers. In some embodiments, such materials comprise crosslinks that utilize amino acid residue side chains (e.g., phenolic side chains). In some embodiments, provided materials comprise enzymatically crosslinked polymers (e.g., silk polymers).

In some embodiments, provided compositions comprise a cell. In some embodiments, a cell is a bone cell (e.g., osteoblast, osteoclast), stem cell (e.g., a human mesenchymal stem cell), and/or chondrocytes. In some embodiments, provided compositions may be configured to support encapsulation of at least one cell. In some embodiments, provided compositions may be configured as a matrix capable of encapsulating a plurality of cells.

In some embodiments, provided materials are configured to support encapsulation of at least one biological or biologically active agent. In some embodiments, provided materials may encapsulate or otherwise comprise at least one biological or biologically active agent. In some embodiments, provided materials that encapsulate or otherwise comprise at least one biological or biologically active agent may release the agent as the material degrades.

In some embodiments, provided materials are configured to support incorporation of and/or modification with one or more additives. In some embodiments, provided materials provide tunable mechanical properties that support encapsulation cells, for example for cell engineering and/or tissue regeneration applications including for example in the treatment or prevention of a disease, disorder or condition and/or for inducing tissue repair.

In some embodiments, the present invention provides methods of providing, preparing, and/or manufacturing crosslinked compositions, for example foams, comprising enzymatically introduced crosslinks. In some embodiments, provided methods of providing, preparing, and/or manufacturing crosslinked compositions comprises introducing crosslinks with peroxidase (e.g., in the presence of peroxide). In some embodiments, a peroxidase selected from the group consisting of animal heme-dependent peroxidase, bromoperoxidase, glutathione peroxidase, haloperoxidase, horseradish peroxidase, lactoperoxidase, myeloperoxidase, thyroid peroxidase, vanadium and combinations thereof. In some embodiments, a peroxidase is utilized at a concentration between about 0.001 mg/mL and about 10 mg/mL (e.g., 0.01 mg/mL to 10 mg/mL, 0.1 mg/mL to 10 mg/mL, 1 mg/mL to 10 mg/mL, etc). In some embodiments, a peroxide is selected from the group consisting of barium peroxide, calcium peroxide, hydrogen peroxide, sodium peroxide, organic peroxides and combinations thereof.

BRIEF DESCRIPTION OF THE DRAWINGS

The foregoing and other objects, aspects, features, and advantages of the present disclosure will become more apparent and better understood by referring to the following description taken in conjunction with the accompanying figures in which:

FIG. 1A shows exemplary starting materials: silk solution, HA powder, horseradish peroxidase (HRP) enzyme, and hydrogen peroxide. FIG. 1B shows that HRP enzyme is first mixed into the silk solution. In FIG. 1C, the silk-HRP solution is then mixed with HA powder to form the substantially homogenous paste of FIG. 1D. As shown in the exemplary process depicted in FIG. 1, hydrogen peroxide is then mixed into the paste as shown in FIG. 1E before the mixture is packed into silicone molds (FIG. 1F) and allowed to sit at room temperature until the setting is complete. FIG. 1G shows the HA-silk foams can be removed from the silicone mold and stored, for example either dry at ambient conditions (depicted in FIG. 1H), or hydrated in water or DMEM (not illustrated) until ready for use (as depicted in FIG. 1I).

FIG. 2A shows that some embodiments exhibit significant flexibility under compressive stress, and FIG. 2B shows that some embodiments are resilient under conditions of flexure stress (e.g., bending).

As shown in FIG. 3, compositions formed without the use of a substrate to facilitate, here, enzymatic crosslinking, were unable to bear compressive stress without fragmentation. FIG. 3A shows that compositions made according to prior methods exhibited formation of visible cracks in the matrix of the silk-HA-HRP paste after 5 minutes of setting. FIG. 3B depicts exemplary attempts to remove the composition from a mold, which resulted in fragmentation of the composition (also shown in FIG. 3C).

As shown in FIG. 6A, in some embodiments, a 30-minute boil, 6% wt/v silk may produce a composition with a slightly higher Young's Modulus than the 60-minute boil, 6% wt/v silk. As shown in FIG. 6B, in some embodiments, a higher powder to liquid (P/L) ratio may result in compositions with a higher Young's Modulus as compared to compositions with a lower P/L ratio. FIG. 6C depicts exemplary effects of increasing the HRP/silk ratio on the Young's Modulus of certain embodiments. In each of the above cases, the concentration of silk solution used in forming the foam was 6% wt/v.

FIG. 7 shows cyclic compression curves obtained by subjecting provided HA-silk foams to 35% strain under confined compression. Specifically, FIG. 7A shows the effect of silk boil time on the ability of certain embodiments to recover after 35% compressive strain. FIG. 7B shows exemplary effects of altering the powder-to-liquid-ratio on recovery behavior of certain embodiments. FIG. 7C depicts exemplary effects of altering the ratio of HRP to silk on recovery behavior of certain embodiments.

FIG. 8A depicts the effect of altering silk boil times on the storage modulus of some embodiments. FIG. 8B depicts exemplary effects of altering the powder-to-liquid-ratio on the storage modulus of certain embodiments. FIG. 8C shows certain exemplary effects of altering the ratio of HRP to silk on the storage modulus of some embodiments.

FIG. 12A depicts hMSC survival and proliferation on HA-silk foams over a 12-day culture period using Alamar blue metabolic assay.

FIG. 12B depicts live/dead staining and confocal microscopy imaging of hMSCs seeded on the surface of HA-silk foams to visualize cell viability and cell distribution. TCP=tissue culture plastic, a control condition including no scaffold which demonstrates baseline growth rate for hMSCs in culture as compared to the growth rate on provided scaffolds. Scale bars are 300 μm.

DEFINITIONS

Figure 1:
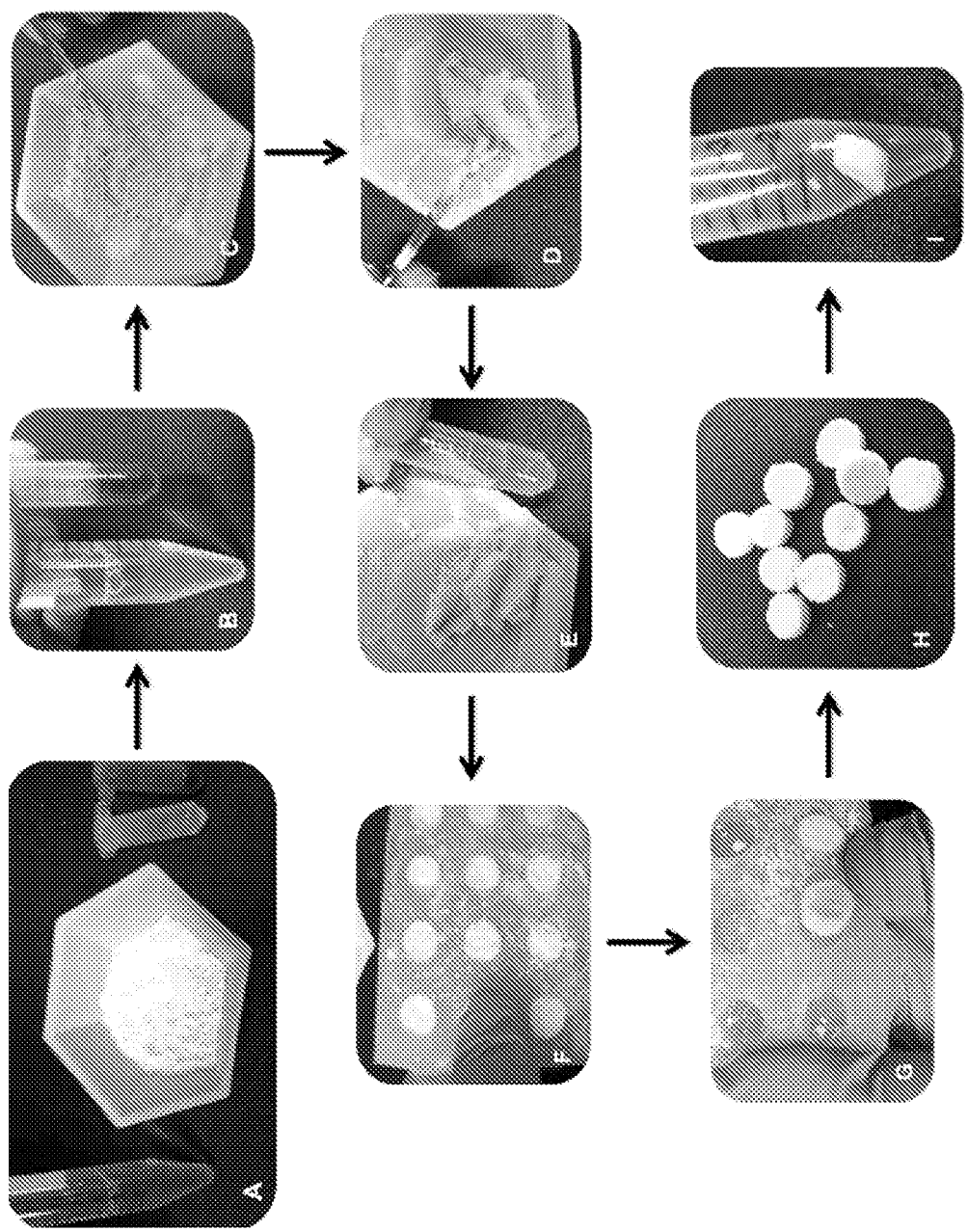
FIG. 1 depicts a flow chart showing, inter alia, an exemplary process for making injectable, flexible HA-silk foam scaffolds. Panel

In order for the present disclosure to be more readily understood, certain terms are first defined below. Additional definitions for the following terms and other terms are set forth throughout the specification.

In this application, unless otherwise clear from context, the term "a" may be understood to mean "at least one." As used in this application, the term "or" may be understood to mean "and/or." In this application, the terms "comprising" and "including" may be understood to encompass itemized components or steps whether presented by themselves or together with one or more additional components or steps. Where ranges are provided herein, the endpoints are included. As used in this application, the term "comprise" and variations of the term, such as "comprising" and "comprises," are not intended to exclude other additives, components, integers or steps.

As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

"Administration": As used herein, the term "administration" refers to the administration of a composition to a subject. Administration may be by any appropriate route. For example, in some embodiments, administration may be bronchial (including by bronchial instillation), enteral, interdermal, intradermal, intramedullary, intramuscular, intraperitoneal, intrathecal, intravenous, intraventricular, mucosal, nasal, rectal, subcutaneous, topical, transdermal, vaginal and vitreal.

"Amino acid": As used herein, the term "amino acid," in its broadest sense, refers to any compound and/or substance that can be incorporated into a polypeptide chain, e.g., through formation of one or more peptide bonds. In some embodiments, an amino acid has the general structure H2N—C(H)(R)—COOH. In some embodiments, an amino acid is a naturally-occurring amino acid. In some embodiments, an amino acid is a synthetic amino acid; in some embodiments, an amino acid is a D-amino acid; in some embodiments, an amino acid is an L-amino acid. "Standard amino acid" refers to any of the twenty standard L-amino acids commonly found in naturally occurring peptides. "Nonstandard amino acid" refers to any amino acid, other than the standard amino acids, regardless of whether it is prepared synthetically or obtained from a natural source. In some embodiments, an amino acid, including a carboxy- and/or amino-terminal amino acid in a polypeptide, can contain a structural modification as compared with the general structure above. For example, in some embodiments, an amino acid may be modified by methylation, amidation, acetylation, and/or substitution as compared with the general structure. In some embodiments, such modification may, for example, alter the circulating half-life of a polypeptide containing the modified amino acid as compared with one containing an otherwise identical unmodified amino acid. In some embodiments, such modification does not significantly alter a relevant activity of a polypeptide containing the modified amino acid, as compared with one containing an otherwise identical unmodified amino acid. As will be clear from context, in some embodiments, the term "amino acid" is used to refer to a free amino acid; in some embodiments it is used to refer to an amino acid residue of a polypeptide.

"Associated": As used herein, the term "associated" typically refers to two or more entities in physical proximity with one another, either directly or indirectly (e.g., via one or more additional entities that serve as a linking agent), to form a structure that is sufficiently stable so that the entities remain in physical proximity under relevant conditions, e.g., physiological conditions. In some embodiments, associated entities are covalently linked to one another. In some embodiments, associated entities are non-covalently linked. In some embodiments, associated entities are linked to one another by specific non-covalent interactions (i.e., by interactions between interacting ligands that discriminate between their interaction partner and other entities present in the context of use, such as, for example. streptavidin/avidin interactions, antibody/antigen interactions, etc.). Alternatively or additionally, a sufficient number of weaker non-covalent interactions can provide sufficient stability for moieties to remain associated. Exemplary non-covalent interactions include, but are not limited to, affinity interactions, metal coordination, physical adsorption, host-guest interactions, hydrophobic interactions, pi stacking interactions, hydrogen bonding interactions, van der Waals interactions, magnetic interactions, electrostatic interactions, dipole-dipole interactions, etc.

"Biocompatible": The term "biocompatible", as used herein, refers to materials that do not cause significant harm to living tissue when placed in contact with such tissue, e.g., in vivo. In certain embodiments, materials are "biocompatible" if they are not toxic to cells. In certain embodiments, materials are "biocompatible" if their addition to cells in vitro results in less than or equal to 20% cell death, and/or their administration in vivo does not induce significant inflammation or other such adverse effects.

"Biodegradable": As used herein, the term "biodegradable" refers to materials that, when introduced into cells, are broken down (e.g., by cellular machinery, such as by enzymatic degradation, by hydrolysis, and/or by combinations thereof) into components that cells can either reuse or dispose of without significant toxic effects on the cells. In certain embodiments, components generated by breakdown of a biodegradable material are biocompatible and therefore do not induce significant inflammation and/or other adverse effects in vivo. In some embodiments, biodegradable polymer materials break down into their component monomers. In some embodiments, breakdown of biodegradable materials (including, for example, biodegradable polymer materials) involves hydrolysis of ester bonds. Alternatively or additionally, in some embodiments, breakdown of biodegradable materials (including, for example, biodegradable polymer materials) involves cleavage of urethane linkages. Exemplary biodegradable polymers include, for example, polymers of hydroxy acids such as lactic acid and glycolic acid, including but not limited to poly(hydroxyl acids), poly(lactic acid)(PLA), poly(glycolic acid)(PGA), poly(lactic-co-glycolic acid)(PLGA), and copolymers with PEG, polyanhydrides, poly(ortho)esters, polyesters, polyurethanes, poly(butyric acid), poly(valeric acid), poly(caprolactone), poly(hydroxyalkanoates, poly(lactide-co-caprolactone), blends and copolymers thereof. Many naturally occurring polymers are also biodegradable, including, for example, proteins such as albumin, collagen, gelatin and prolamines, for example, zein, and polysaccharides such as alginate, cellulose derivatives and polyhydroxyalkanoates, for example, polyhydroxybutyrate blends and copolymers thereof. Those of ordinary skill in the art will appreciate or be able to determine when such polymers are biocompatible and/or biodegradable derivatives thereof (e.g., related to a parent polymer by substantially identical structure that differs only in substitution or addition of particular chemical groups as is known in the art).

"Comparable": The term "comparable", as used herein, refers to two or more agents, entities, situations, sets of conditions, etc. that may not be identical to one another but that are sufficiently similar to permit comparison there between so that conclusions may reasonably be drawn based on differences or similarities observed. Those of ordinary skill in the art will understand, in context, what degree of identity is required in any given circumstance for two or more such agents, entities, situations, sets of conditions, etc. to be considered comparable.

"Conjugated": As used herein, the terms "conjugated," "linked," "attached," and "associated with," when used with respect to two or more moieties, means that the moieties are physically associated or connected with one another, either directly or via one or more additional moieties that serves as a linking agent, to form a structure that is sufficiently stable so that the moieties remain physically associated under the conditions in which structure is used, e.g., physiological conditions. Typically the moieties are attached either by one or more covalent bonds or by a mechanism that involves specific binding. Alternately, a sufficient number of weaker interactions can provide sufficient stability for moieties to remain physically associated.

"Corresponding to": As used herein, the term "corresponding to" is often used to designate the position/identity of a residue in a polymer, such as an amino acid residue in a polypeptide or a nucleotide residue in a nucleic acid. Those of ordinary skill will appreciate that, for purposes of simplicity, residues in such a polymer are often designated using a canonical numbering system based on a reference related polymer, so that a residue in a first polymer "corresponding to" a residue at position 190 in the reference polymer, for example, need not actually be the 190th residue in the first polymer but rather corresponds to the residue found at the 190th position in the reference polymer; those of ordinary skill in the art readily appreciate how to identify "corresponding" amino acids, including through use of one or more commercially-available algorithms specifically designed for polymer sequence comparisons.

"Dosage form": As used herein, the term "dosage form" refers to a physically discrete unit of a therapeutic agent for administration to a subject. Each unit contains a predetermined quantity of active agent. In some embodiments, such quantity is a unit dosage amount (or a whole fraction thereof) appropriate for administration in accordance with a dosing regimen that has been determined to correlate with a desired or beneficial outcome when administered to a relevant population (i.e., with a therapeutic dosing regimen).

"Encapsulated": The term "encapsulated" is used herein to refer to substances that are substantially completely surrounded by another material.

"Functional": As used herein, a "functional" biological molecule is a biological molecule in a form in which it exhibits a property and/or activity by which it is characterized. A biological molecule may have two functions (i.e., bi-functional) or many functions (i.e., multifunctional).

"Graft rejection": The term "graft rejection" as used herein, refers to rejection of tissue transplanted from a donor individual to a recipient individual. In some embodiments, graft rejection refers to an allograft rejection, wherein the donor individual and recipient individual are of the same species. Typically, allograft rejection occurs when the donor tissue carries an alloantigen against which the recipient immune system mounts a rejection response.

"High Molecular Weight Polymer": As used herein, the term "high molecular weight polymer" refers to polymers and/or polymer solutions comprised of polymers (e.g., protein polymers, such as silk) having molecular weights of at least about 200 kDa, and wherein no more than 30% of the silk fibroin has a molecular weight of less than 100 kDa. In some embodiments, high molecular weight polymers and/or polymer solutions have an average molecular weight of at least about 100 kDa or more, including, e.g., at least about 150 kDa, at least about 200 kDa, at least about 250 kDa, at least about 300 kDa, at least about 350 kDa or more. In some embodiments, high molecular weight polymers have a molecular weight distribution, no more than 50%, for example, including, no more than 40%, no more than 30%, no more than 20%, no more than 10%, of the silk fibroin can have a molecular weight of less than 150 kDa, or less than 125 kDa, or less than 100 kDa.

"Hydrolytically degradable": As used herein, the term "hydrolytically degradable" is used to refer to materials that degrade by hydrolytic cleavage. In some embodiments, hydrolytically degradable materials degrade in water. In some embodiments, hydrolytically degradable materials degrade in water in the absence of any other agents or materials. In some embodiments, hydrolytically degradable materials degrade completely by hydrolytic cleavage, e.g., in water. By contrast, the term "non-hydrolytically degradable" typically refers to materials that do not fully degrade by hydrolytic cleavage and/or in the presence of water (e.g., in the sole presence of water).

"Hydrophilic": As used herein, the term "hydrophilic" and/or "polar" refers to a tendency to mix with, or dissolve easily in, water.

"Hydrophobic": As used herein, the term "hydrophobic" and/or "non-polar", refers to a tendency to repel, not combine with, or an inability to dissolve easily in, water.

"Low Molecular Weight Polymer": As used herein, the term "low molecular weight polymer" refers to polymers and/or polymer solutions, such as silk, comprised of polymers (e.g., protein polymers) having molecular weights within the range of about 20 kDa-about 400 kDa. In some embodiments, low molecular weight polymers (e.g., protein polymers) have molecular weights within a range between a lower bound (e.g., about 20 kDa, about 30 kDa, about 40 kDa, about 50 kDa, about 60 kDa, or more) and an upper bound (e.g., about 400 kDa, about 375 kDa, about 350 kDa, about 325 kDa, about 300 kDa, or less). In some embodiments, low molecular weight polymers (e.g., protein polymers such as silk) are substantially free of polymers having a molecular weight above about 400 kD. In some embodiments, the highest molecular weight polymers in provided hydrogels are less than about 300-about 400 kD (e.g., less than about 400 kD, less than about 375 kD, less than about 350 kD, less than about 325 kD, less than about 300 kD, etc). In some embodiments, a low molecular weight polymer and/or polymer solution can comprise a population of polymer fragments having a range of molecular weights, characterized in that: no more than 15% of the total moles of polymer fragments in the population has a molecular weight exceeding 200 kDa, and at least 50% of the total moles of the silk fibroin fragments in the population has a molecular weight within a specified range, wherein the specified range is between about 3.5 kDa and about 120 kDa or between about 5 kDa and about 125 kDa.

"Nucleic acid": As used herein, the term "nucleic acid," in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. In some embodiments, "nucleic acid" refers to individual nucleic acid residues (e.g., nucleotides and/or nucleosides). In some embodiments, "nucleic acid" refers to an oligonucleotide chain comprising individual nucleic acid residues. As used herein, the terms "oligonucleotide" and "polynucleotide" can be used interchangeably. In some embodiments, "nucleic acid" encompasses RNA as well as single and/or double-stranded DNA and/or cDNA. Furthermore, the terms "nucleic acid," "DNA," "RNA," and/or similar terms include nucleic acid analogs, i.e., analogs having other than a phosphodiester backbone. For example, the so-called "peptide nucleic acids," which are known in the art and have peptide bonds instead of phosphodiester bonds in the backbone, are considered within the scope of the present invention. The term "nucleotide sequence encoding an amino acid sequence" includes all nucleotide sequences that are degenerate versions of each other and/or encode the same amino acid sequence. Nucleotide sequences that encode proteins and/or RNA may include introns. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, backbone modifications, etc. A nucleic acid sequence is presented in the 5' to 3' direction unless otherwise indicated. The term "nucleic acid segment" is used herein to refer to a nucleic acid sequence that is a portion of a longer nucleic acid sequence. In many embodiments, a nucleic acid segment comprises at least 3, 4, 5, 6, 7, 8, 9, 10, or more residues. In some embodiments, a nucleic acid is or comprises natural nucleosides (e.g., adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages). In some embodiments, the present invention is specifically directed to "unmodified nucleic acids," meaning nucleic acids (e.g., polynucleotides and residues, including nucleotides and/or nucleosides) that have not been chemically modified in order to facilitate or achieve delivery.

"Pharmaceutical composition": As used herein, the term "pharmaceutical composition" refers to an active agent, formulated together with one or more pharmaceutically acceptable carriers. In some embodiments, active agent is present in unit dose amount appropriate for administration in a therapeutic regimen that shows a statistically significant probability of achieving a predetermined therapeutic effect when administered to a relevant population. In some embodiments, pharmaceutical compositions may be specially formulated for administration in solid or liquid form, including those adapted for the following: tablets, boluses, powders, granules, pastes; parenteral administration, for example, by subcutaneous, intramuscular, intravenous or epidural injection as, for example, a sterile solution or suspension, or sustained-release formulation; topical application, for example, as a cream, ointment, or a controlled-release patch or spray applied to the skin or oral cavity; intravaginally or intrarectally, for example, as a pessary, cream, or foam; sublingually; ocularly; transdermally; or nasally, pulmonary, and to other mucosal surfaces.

"Physiological conditions": The phrase "physiological conditions", as used herein, relates to the range of chemical (e.g., pH, ionic strength) and biochemical (e.g., enzyme concentrations) conditions likely to be encountered in the intracellular and extracellular fluids of tissues. For most tissues, the physiological pH ranges from about 6.8 to about 8.0 and a temperature range of about 20-40 degrees Celsius, about 25-40° C., about 30-40° C., about 35-40° C., about 37° C., and atmospheric pressure of about 1. In some embodiments, physiological conditions utilize or include an aqueous environment (e.g., water, saline, Ringers solution, or other buffered solution); in some such embodiments, the aqueous environment is or comprises a phosphate buffered solution (e.g., phosphate-buffered saline).

"Polypeptide": The term "polypeptide" as used herein, refers to a string of at least three amino acids linked together by peptide bonds. In some embodiments, a polypeptide comprises naturally-occurring amino acids; alternatively or additionally, in some embodiments, a polypeptide comprises one or more non-natural amino acids (i.e., compounds that do not occur in nature but that can be incorporated into a polypeptide chain; see, for example, www.cco.caltech.edu/~dadgrp/Unnatstruct.gif, which displays structures of non-natural amino acids that have been successfully incorporated into functional ion channels) and/or amino acid analogs as are known in the art may alternatively be employed). For example, a polypeptide can be a protein. In some embodiments, one or more of the amino acids in a polypeptide may be modified, for example, by the addition of a chemical entity such as a carbohydrate group, a phosphate group, a farnesyl group, an isofarnesyl group, a fatty acid group, a linker for conjugation, functionalization, or other modification, etc.

"Polysaccharide": The term "polysaccharide" refers to a polymer of sugars. Typically, a polysaccharide comprises at least three sugars. In some embodiments, a polypeptide comprises natural sugars (e.g., glucose, fructose, galactose, mannose, arabinose, ribose, and xylose); alternatively or additionally, in some embodiments, a polypeptide comprises one or more non-natural amino acids (e.g. modified sugars such as 2'-fluororibose, 2'-deoxyribose, and hexose).

"Porosity": The term "porosity" as used herein, refers to a measure of void spaces in a material and is a fraction of volume of voids over the total volume, as a percentage between 0 and 100%. A determination of porosity is known to a skilled artisan using standardized techniques, for example mercury porosimetry and gas adsorption (e.g., nitrogen adsorption).

"Protein": As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids. In some embodiments, proteins are antibodies, antibody fragments, biologically active portions thereof, and/or characteristic portions thereof.

"Small molecule": As used herein, the term "small molecule" is used to refer to molecules, whether naturally-occurring or artificially created (e.g., via chemical synthesis), having a relatively low molecular weight and being an organic and/or inorganic compound. Typically, a "small molecule" is monomeric and have a molecular weight of less than about 1500 g/mol. In general, a "small molecule" is a molecule that is less than about 5 kilodaltons (kD) in size. In some embodiments, a small molecule is less than about 4 kD, 3 kD, about 2 kD, or about 1 kD. In some embodiments, the small molecule is less than about 800 daltons (D), about 600 D, about 500 D, about 400 D, about 300 D, about 200 D, or about 100 D. In some embodiments, a small molecule is less than about 2000 g/mol, less than about 1500 g/mol, less than about 1000 g/mol, less than about 800 g/mol, or less than about 500 g/mol. In some embodiments, a small molecule is not a polymer. In some embodiments, a small molecule does not include a polymeric moiety. In some embodiments, a small molecule is not a protein or polypeptide (e.g., is not an oligopeptide or peptide). In some embodiments, a small molecule is not a polynucleotide (e.g., is not an oligonucleotide). In some embodiments, a small molecule is not a polysaccharide. In some embodiments, a small molecule does not comprise a polysaccharide (e.g., is not a glycoprotein, proteoglycan, glycolipid, etc.). In some embodiments, a small molecule is not a lipid. In some embodiments, a small molecule is a modulating agent. In some embodiments, a small molecule is biologically active. In some embodiments, a small molecule is detectable (e.g., comprises at least one detectable moiety). In some embodiments, a small molecule is a therapeutic. Preferred small molecules are biologically active in that they produce a local or systemic effect in animals, preferably mammals, more preferably humans. In certain preferred embodiments, the small molecule is a drug. Preferably, though not necessarily, the drug is one that has already been deemed safe and effective for use by the appropriate governmental agency or body. For example, drugs for human use listed by the FDA under 21 C.F.R. §§ 330.5, 331 through 361, and 440 through 460; drugs for veterinary use listed by the FDA under 21 C.F.R. §§ 500 through 589, incorporated herein by reference, are all considered acceptable for use in accordance with the present application.

"Solution": As used herein, the term "solution" broadly refers to a homogeneous mixture composed of one phase. Typically, a solution comprises a solute or solutes dissolved in a solvent or solvents. It is characterized in that the properties of the mixture (such as concentration, temperature, and density) can be uniformly distributed through the volume. In the context of the present application, therefore, a "silk fibroin solution" refers to silk fibroin protein in a soluble form, dissolved in a solvent, such as water. In some embodiments, silk fibroin solutions may be prepared from a solid-state silk fibroin material (i.e., silk matrices), such as silk films and other scaffolds. Typically, a solid-state silk fibroin material is reconstituted with an aqueous solution, such as water and a buffer, into a silk fibroin solution. It should be noted that liquid mixtures that are not homogeneous, e.g., colloids, suspensions, emulsions, are not considered solutions.

"Stable": The term "stable," when applied to compositions herein, means that the compositions maintain one or more aspects of their physical structure and/or activity over a period of time under a designated set of conditions. In some embodiments, a period of time is at least about one hour; in some embodiments, the period of time is about 5 hours, about 10 hours, about one (1) day, about one (1) week, about two (2) weeks, about one (1) month, about two (2) months, about three (3) months, about four (4) months, about five (5) months, about six (6) months, about eight (8) months, about ten (10) months, about twelve (12) months, about twenty-four (24) months, about thirty-six (36) months, or longer. In some embodiments, the period of time is within the range of about one (1) day to about twenty-four (24) months, about two (2) weeks to about twelve (12) months, about two (2) months to about five (5) months, etc. In some embodiments, the designated conditions are ambient conditions (e.g., at room temperature and ambient pressure). In some embodiments, the designated conditions are physiologic conditions (e.g., in vivo or at about 37° C. for example in serum or in phosphate buffered saline). In some embodiments, the designated conditions are under cold storage (e.g., at or below about 4° C., −20° C., or −70° C.). In some embodiments, the designated conditions are in the dark.

"Substantially": As used herein, the term "substantially", and grammatical equivalents, refer to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result.

"Sustained release": The term "sustained release" is used herein in accordance with its art-understood meaning of release that occurs over an extended period of time. The extended period of time can be at least about 3 days, about 5 days, about 7 days, about 10 days, about 15 days, about 30 days, about 1 month, about 2 months, about 3 months, about 6 months, or even about 1 year. In some embodiments, sustained release is substantially burst-free. In some embodiments, sustained release involves steady release over the extended period of time, so that the rate of release does not vary over the extended period of time more than about 5%, about 10%, about 15%, about 20%, about 30%, about 40% or about 50%. In some embodiments, sustained release involves release with first-order kinetics. In some embodiments, sustained release involves an initial burst, followed by a period of steady release. In some embodiments, sustained release does not involve an initial burst. In some embodiments, sustained release is substantially burst-free release.

"Therapeutic agent": As used herein, the phrase "therapeutic agent" refers to any agent that elicits a desired pharmacological effect when administered to an organism. In some embodiments, an agent is considered to be a therapeutic agent if it demonstrates a statistically significant effect across an appropriate population. In some embodiments, the appropriate population may be a population of model organisms. In some embodiments, an appropriate population may be defined by various criteria, such as a certain age group, gender, genetic background, preexisting clinical conditions, etc. In some embodiments, a therapeutic agent is any substance that can be used to alleviate, ameliorate, relieve, inhibit, prevent, delay onset of, reduce severity of, and/or reduce incidence of one or more symptoms or features of a disease, disorder, and/or condition.

"Treating": As used herein, the term "treating" refers to partially or completely alleviating, ameliorating, relieving, inhibiting, preventing (for at least a period of time), delaying onset of, reducing severity of, reducing frequency of and/or reducing incidence of one or more symptoms or features of a particular disease, disorder, and/or condition. In some embodiments, treatment may be administered to a subject who does not exhibit symptoms, signs, or characteristics of a disease and/or exhibits only early symptoms, signs, and/or characteristics of the disease, for example for the purpose of decreasing the risk of developing pathology associated with the disease. In some embodiments, treatment may be administered after development of one or more symptoms, signs, and/or characteristics of the disease.

DETAILED DESCRIPTION OF CERTAIN EMBODIMENTS

The present invention provides, inter alia, methods and compositions comprising silk and one or more inorganic materials (e.g., calcium phosphate material). In some embodiments, provided methods and compositions may be used in orthopedic and/or dental applications, for example, as a bone or other tissue replacement. According to various embodiments, provided compositions represent a new class of materials comprising a crosslinked silk fibroin, at least one inorganic material, for example, a calcium phosphate material. According to various embodiments, provided compositions have a previously unattainable level of inorganic material in the solid portion of certain provided compositions. In some embodiments, greater than 80% (e.g., 85%, 90%, 95%, 99%) of the solids in a particular composition are or comprise inorganic material.

While the fiber form of silk has used in suture or textile-based applications, solubilized silk fibroin allows the creation of unique three-dimensional morphologies and materials for applications that range beyond the traditional textile-based applications. Solubilized silk (e.g., a silk solution) can be processed to create a range of material formats, including, but not limited to, films, foams, fibers, gels, and sponges. Provided herein, among other things, are novel methods for forming silk fibroin compositions. In some embodiments, provided compositions are or comprise a foam. In some embodiments, a foam is an open-cell foam. In some embodiments, a foam is a closed-cell foam.

In some embodiments, the present invention provides methods of producing silk ceramic compositions/materials including the steps of subjecting a composition comprising silk fibroin and a calcium phosphate material to enzymatic crosslinking under conditions and for a period of time sufficient to convert the material from a first state that is substantially free of beta sheet character with no solid form structure to a second state having significant beta sheet character, the composition being characterized in that an otherwise comparable composition lacking the calcium phosphate and comparably exposed to enzymatic crosslinking under the conditions and for the period of time does not produce a material state with such beta sheet content and with such stiffness, toughness, and mechanical rigidity.

In some embodiments, the first state is or comprises a substantially aqueous solution or powder. In some embodiments, the silk present in the first state exhibits substantially no beta sheet character. In some embodiments, the second state is or comprises a foam. In some embodiments, the silk present in the second state exhibits significant beta sheet character (e.g., more than 70%, 80%, 90%, or 95% of the silk exhibits beta sheet structure).

Silk and Silk Solutions

Silk is a natural protein fiber produced in a specialized gland of certain organisms. Silk production in organisms is especially common in the Hymenoptera (bees, wasps, and ants), and is sometimes used in nest construction. Other types of arthropod also produce silk, most notably various arachnids such as spiders (e.g., spider silk). Silk fibers generated by insects and spiders represent the strongest natural fibers known and rival even synthetic high performance fibers.

Silk has been a highly desired and widely used textile since its first appearance in ancient China (see Elisseeff, "The Silk Roads: Highways of Culture and Commerce," Berghahn Books/UNESCO, New York (2000); see also Vainker, "Chinese Silk: A Cultural History," Rutgers University Press, Piscataway, N.J. (2004)). Glossy and smooth, silk is favored by not only fashion designers but also tissue engineers because it is mechanically tough but degrades harmlessly inside the body, offering new opportunities as a highly robust and biocompatible material substrate (see Altman et al., Biomaterials, 24: 401 (2003); see also Sashina et al., Russ. J. Appl. Chem., 79: 869 (2006)).

Silk is naturally produced by various species, including, without limitation: *Antheraea mylitta*; *Antheraea pernyi*; *Antheraea yamamai*; *Galleria mellonella*; *Bombyx mori*; *Bombyx mandarina*; *Galleria mellonella*; *Nephila clavipes*; *Nephila senegalensis*; *Gasteracantha mammosa*; *Argiope aurantia*; *Araneus diadematus*; *Latrodectus geometricus*; *Araneus bicentenarius*; *Tetragnatha versicolor*; *Araneus ventricosus*; *Dolomedes tenebrosus*; *Euagrus chisoseus*; *Plectreurys tristis*; *Argiope trifasciata*; and *Nephila madagascariensis*.

In general, silk for use in accordance with various embodiments may be produced by any such organism, or may be prepared through an artificial process, for example, involving genetic engineering of cells or organisms to produce a silk protein and/or chemical synthesis. In some embodiments, silk is produced by the silkworm, *Bombyx mori*. As is known in the art, silks are modular in design, with large internal repeats flanked by shorter (~100 amino acid) terminal domains (N and C termini). Silks have high molecular weight (200 to 350 kDa or higher) with transcripts of 10,000 base pairs and higher and >3000 amino acids (reviewed in Omenetto and Kaplan (2010) Science 329: 528-531). The larger modular domains are interrupted with relatively short spacers with hydrophobic charge groups in the case of silkworm silk. N- and C-termini are involved in the assembly and processing of silks, including pH control of assembly. The N- and C-termini are highly conserved, in spite of their relatively small size compared with the internal modules.

Silk Fibroin

Fibroin is a type of structural protein produced by certain spider and insect species that produce silk. Cocoon silk produced by the silkworm, *Bombyx mori*, is of particular interest because it offers low-cost, bulk-scale production suitable for a number of commercial applications, such as in various textiles.

Silkworm cocoon silk contains two structural proteins, the fibroin heavy chain (~350 kDa) and the fibroin light chain (~25 kDa), which are associated with a family of non-structural proteins termed sericin, which glue the fibroin brings together in forming the cocoon. The heavy and light chains of fibroin are linked by a disulfide bond at the C-terminus of the two subunits (see Takei, F., Kikuchi, Y., Kikuchi, A., Mizuno, S. and Shimura, K. (1987) 105 J. Cell Biol., 175-180; see also Tanaka, K., Mori, K. and Mizuno, S. 114 J. Biochem. (Tokyo), 1-4 (1993); Tanaka, K., Kajiyama, N., Ishikura, K., Waga, S., Kikuchi, A., Ohtomo, K., Takagi, T. and Mizuno, S., 1432 Biochim. Biophys. Acta., 92-103 (1999); Y Kikuchi, K Mori, S Suzuki, K Yamaguchi and S Mizuno, "Structure of the *Bombyx mori* fibroin light-chain-encoding gene: upstream sequence elements common to the light and heavy chain," 110 Gene, 151-158 (1992)). The sericins are a high molecular weight, soluble glycoprotein constituent of silk which gives the stickiness to the material. These glycoproteins are hydrophilic and can be easily removed from cocoons by boiling in water.

As used herein, the term "silk fibroin" refers to silk fibroin protein, whether produced by silkworm, spider, or other insect, or otherwise generated (Lucas et al., 13 Adv. Protein Chem., 107-242 (1958)). In some embodiments, silk fibroin is obtained from a solution containing a dissolved silkworm silk or spider silk. For example, in some embodiments, silkworm silk fibroins are obtained, from the cocoon of *Bombyx mori*. In some embodiments, spider silk fibroins are obtained, for example, from *Nephila clavipes*. In the alternative, in some embodiments, silk fibroins suitable for use in the invention are obtained from a solution containing a genetically engineered silk harvested from bacteria, yeast, mammalian cells, transgenic animals or transgenic plants. See, e.g., WO 97/08315 and U.S. Pat. No. 5,245,012, each of which is incorporated herein as reference in its entirety.

Thus, in some embodiments, a silk solution is used to fabricate compositions of the present invention containing fibroin proteins, essentially free of sericins. In some embodiments, silk solutions used to fabricate various compositions of the present invention contain the heavy chain of fibroin, but are essentially free of other proteins. In other embodiments, silk solutions used to fabricate various compositions of the present invention contain both the heavy and light chains of fibroin, but are essentially free of other proteins. In certain embodiments, silk solutions used to fabricate various compositions of the present invention comprise both a heavy and a light chain of silk fibroin; in some such embodiments, the heavy chain and the light chain of silk fibroin are linked via at least one disulfide bond. In some embodiments where the heavy and light chains of fibroin are present, they are linked via one, two, three or more disulfide bonds. Although different species of silk-producing organisms, and different types of silk, have different amino acid compositions, various fibroin proteins share certain structural features. A general trend in silk fibroin structure is a sequence of amino acids that is characterized by usually alternating glycine and alanine, or alanine alone. Such configuration allows fibroin molecules to self-assemble into a beta-sheet conformation. These "Ala-rich" hydrophobic blocks are typically separated by segments of amino acids with bulky side-groups (e.g., hydrophilic spacers).

In some embodiments, provided compositions may comprise silk materials prepared from material spun by silkworm, *Bombyx mori*. Typically, cocoons are boiled for ~30 min in an aqueous solution of 0.02 M $Na_2CO_3$, then rinsed thoroughly with water to extract the glue-like sericin proteins. Extracted silk may then be dissolved in a solvent, for example, a LiBr (such as 9.3 M) solution at room temperature. According to various embodiments, a resulting silk fibroin solution may then be further processed for a variety of applications as described elsewhere herein.

In some embodiments, silk proteins/polymers refers to peptide chains or polypeptides having an amino acid sequence corresponding to fragments derived from silk fibroin protein or variants thereof. In the context of certain provided compositions, silk fibroin fragments may generally refer to silk fibroin peptide chains or polypeptides that are smaller than naturally occurring full length silk fibroin counterpart, such that one or more of the silk fibroin fragments within a population or composition are less than 500 kDa, less than 450 kDa, less than 400 kDa, less than 350 kDa, less than 300 kDa, less than 250 kDa, less than 200 kDa, less than 175 kDa, less than 150 kDa, less than 120 kDa, less than 100 kDa, less than 90 kDa, less than 80 kDa, less than 70 kDa, less than 60 kDa, less than 50 kDa, less than 40 kDa, less than 30 kDa, less than 25 kDa, less than 20 kDa, less than 15 kDa, less than 12 kDa, less than 10 kDa, less than 9 kDa, less than 8 kDa, less than 7 kDa, less than 6 kDa, less than 5 kDa, less than 4 kDa, less than 3.5 kDa, less than 3 kDa, less than 2.5 kDa, less than 2 kDa, less than 1.5 kDa, or less than about 1.0 kDa, etc.

In some embodiments, polymers of silk fibroin fragments may be derived by degumming silk cocoons at or close to (e.g., within 5% around) an atmospheric boiling temperature for at least about: 1 minute of boiling, 2 minutes of boiling, 3 minutes of boiling, 4 minutes of boiling, 5 minutes of boiling, 6 minutes of boiling, 7 minutes of boiling, 8 minutes of boiling, 9 minutes of boiling, 10 minutes of boiling, 11 minutes of boiling, 12 minutes of boiling, 13 minutes of boiling, 14 minutes of boiling, 15 minutes of boiling, 16 minutes of boiling, 17 minutes of boiling, 18 minutes of boiling, 19 minutes of boiling, 20 minutes of boiling, 25 minutes of boiling, 30 minutes of boiling, 35 minutes of boiling, 40 minutes of boiling, 45 minutes of boiling, 50 minutes of boiling, 55 minutes of boiling, 60 minutes or longer, including, e.g., at least 70 minutes, at least 80 minutes, at least 90 minutes, at least 100 minutes, at least 110 minutes, at least about 120 minutes or longer. As used herein, the term "atmospheric boiling temperature" refers to a temperature at which a liquid boils under atmospheric pressure.

In some embodiments, compositions of the present invention produced from silk fibroin fragments may be formed by degumming silk cocoons in an aqueous solution at temperatures of: about 30° C., about 35° C., about 40° C., about 45° C., about 50° C., about 45° C., about 60° C., about 65° C., about 70° C., about 75° C., about 80° C., about 85° C., about 90° C., about 95° C., about 100° C., about 105° C., about 110° C., about 115° C., about at least 120° C.

In some embodiments, elevated temperatures may be achieved by carrying out at least portion of the heating process (e.g., boiling process) under pressure. For example, suitable pressure under which silk fibroin fragments described herein can be produced are typically between about 10-40 psi, e.g., about 11 psi, about 12 psi, about 13 psi, about 14 psi, about 15 psi, about 16 psi, about 17 psi, about 18 psi, about 19 psi, about 20 psi, about 21 psi, about 22 psi, about 23 psi, about 24 psi, about 25 psi, about 26 psi, about 27 psi, about 28 psi, about 29 psi, about 30 psi, about 31 psi, about 32 psi, about 33 psi, about 34 psi, about 35 psi, about 36 psi, about 37 psi, about 38 psi, about 39 psi, or about 40 psi.

In some embodiments, silk fibroin fragments may be solubilized prior to formation of provided compositions. In some embodiments, a carrier may be a solvent and/or dispersing medium. In some embodiments, a solvent and/or dispersing medium, for example, is water, cell culture medium, buffers (e.g., phosphate buffered saline), a buffered solution (e.g. PBS), polyol (for example, glycerol, propylene glycol, liquid polyethylene glycol, and the like), Dulbecco's Modified Eagle Medium, fetal bovine serum, or suitable combinations and/or mixtures thereof.

According to various embodiments, any of a variety of silk fibroins and silk fibroin solutions (i.e., silk solutions) may be used in the formation of provided compositions. Silk fibroin, derived from *Bombyx mori* silkworm cocoons, for example, is biocompatible, degrades slowly in the body, is readily modified into a variety of formats and generates mechanically robust materials.

In some embodiments, provided silk compositions, and methods of making and/or using them, may be performed in the absence of any organic solvent. Thus, in some embodiments, provided compositions and methods are particularly amenable to the incorporation of labile molecules, such as bioactive agents or therapeutics, and can, in certain embodiments, be used to produce controlled release biomaterials. In some embodiments, such methods are performed in water only.

A silk fibroin solution can be prepared by any conventional method known to one skilled in the art. According to various embodiments, the solution is an aqueous solution. By way of non-limiting example, *B. mori* cocoons are boiled for about 30 minutes in an aqueous solution. In some embodiments, the aqueous solution is about 0.02M $Na_2CO_3$, and cocoons are rinsed, for example, with water to extract the sericin proteins and the extracted silk is then dissolved in an aqueous salt solution. Exemplary salts useful for this purpose include, but are not limited to, lithium bromide, lithium thiocyanate, calcium nitrate, and/or other chemicals capable of solubilizing silk. In some embodiments, extracted silk is dissolved in about 9-12 M LiBr solution, and the salt is consequently removed using, for example, dialysis.

In some embodiments, a silk solution may then be concentrated using, for example, dialysis against a hygroscopic polymer, for example, PEG, a polyethylene oxide, amylose or sericin. In some embodiments, PEG is of a molecular weight of 8,000-10,000 g/mol and has a concentration of 25-50%. In some embodiments, any dialysis system can be used. In some embodiments, dialysis may be for a time period sufficient to result in a final concentration of aqueous silk solution between 10-30%, for example, dialysis for 2-12 hours.

In some embodiments, biocompatible polymers may also be added to the silk solution to generate composite matrices in the methods and processes of the present invention. Exemplary biocompatible polymers useful in the present invention include, for example, polyethylene oxide (PEO) (U.S. Pat. No. 6,302,848), polyethylene glycol (PEG) (U.S. Pat. No. 6,395,734), collagen (U.S. Pat. No. 6,127,143), fibronectin (U.S. Pat. No. 5,263,992), keratin (U.S. Pat. No. 6,379,690), polyaspartic acid (U.S. Pat. No. 5,015,476), polylysine (U.S. Pat. No. 4,806,355), alginate (U.S. Pat. No. 6,372,244), chitosan (U.S. Pat. No. 6,310,188), chitin (U.S. Pat. No. 5,093,489), hyaluronic acid (U.S. Pat. No. 387,413), pectin (U.S. Pat. No. 6,325,810), polycaprolactone (U.S. Pat. No. 6,337,198), polylactic acid (U.S. Pat. No. 6,267,776), polyglycolic acid (U.S. Pat. No. 5,576,881), polyhydroxyalkanoates (U.S. Pat. No. 6,245,537), dextrans (U.S. Pat. No. 5,902,800), and polyanhydrides (U.S. Pat. No. 5,270,419). In some embodiments, two or more biocompatible polymers can be used.

In accordance with various embodiments, a silk solution may comprise any of a variety of concentrations of silk fibroin. In some embodiments, a silk solution may comprise 0.1 to 50% by weight silk fibroin. In some embodiments, a silk solution may comprise between about 0.5% and 50% (e.g., 0.5% to 45%, 0.5% to 40%, 0.5% to 35%, 0.5% to 30%, 0.5% to 25%, 0.5% to 20%, 0.5% to 15%, 0.5% to 10%, 0.5% to 5%, 0.5% to 1.0%) by weight silk fibroin, inclusive. In some embodiments, a silk solution may comprise at least 0.1% (e.g., at least 0.5%, 1%, 2%, 3%, 4%, 5%, 6%, 7%, 8%, 9%, 10%, 15%, 20%, 25%, 30%, 35%, 40%, 45% or more) by weight silk fibroin. In some embodiments, a silk solution may comprise at most 50% (e.g., at most 45%, 40%, 35%, 30%, 25%, 20%, 15%, 14%, 13%, 12% 11%, 10%, 5%, 4%, 3%, 2%, 1% or less) by weight silk fibroin. In some embodiments, silk solutions comprise 8% silk (w/v) or less.

Inorganic/Calcium Phosphate Materials

According to various embodiments, provided compositions comprise one or more inorganic (e.g., calcium phosphate) materials. Without wishing to be held to a particular theory, the presence of calcium phosphate may make provided silk ceramic foams more robust compared to standard hydrogels formed with horseradish peroxidase. In some embodiments, calcium phosphate material for use in provided compositions (e.g., silk ceramic foams) is selected from, but not limited to: brushite, octacalcium phosphate, tricalcium phosphate, calcium hydrogen phosphate, calcium dihydrogen phosphate, monocalcium phosphate monohydrate, monocalcium phosphate anhydrous, dicalcium phosphate dehydrate, dicalcium phosphate anhydrous, octacalcium phosphate, α-tricalcium phosphate, β-tricalcium phosphate, amorphous calcium phosphate, apatite, calcium-deficient hydroxyapatite, hydroxyapatite, fluorapatite, and any combination thereof. Selected exemplary calcium phosphate materials are shown in Table 1, below:

TABLE 1

Exemplary calcium phosphate materials

| Compound | Ca/P Molar Ratio | Chemical Formula | Abbreviation |
| --- | --- | --- | --- |
| Monocalcium phosphate monohydrate | 0.5 | $Ca(H_2PO_4)_2 \cdot H_2O$ | MCPM |
| Monocalcium phosphate anhydrous | 0.5 | $Ca(H_2PO_4)_2$ | MCPA |
| Dicalcium phosphate dihydrate | 1.0 | $CaHPO_4 \cdot 2H_2O$ | DCPD |
| Dicalcium phosphate anhydrous | 1.0 | $CaHPO_4$ | DCPA |
| Octacalcium phosphate | 1.33 | $Ca_8(HPO_4)_2(PO_4)_4 \cdot 5H_2O$ | OCT |
| α-Tricalcium phosphate | 1.5 | $\alpha\text{-}Ca_3(PO_4)_2$ | α-TCP |
| β-Tricalcium phosphate | 1.5 | $\beta\text{-}Ca_3(PO_4)_2$ | β-TCP |
| Amorphous calcium phosphate | 1.2-2.2 | $Ca_x(PO_4)_y \cdot nH_2O$ | ACP |
| Calcium-deficient hydroxyapatite | 1.5-1.67 | $Ca_{10-x}(HPO_4)_x(PO_4)_{6-x}(OH)_{2-x}$ | CDHA |
| Hydroxyapatite | 1.67 | $Ca_{10}(PO_4)_6(OH)_2$ | HA |
| Fluorapatite | 1.67 | $Ca_{10}(PO_4)_6F_2$ | FA |
| Tetracalcium phosphate | 2.0 | $Ca_4(PO_4)_2O$ | TTCP |

In some embodiments, provided compositions may comprise between 10 and 80 weight percent inorganic (e.g., calcium phosphate) material. In some embodiments, provided compositions may comprise at least 10% (e.g., at least 15%, 20%, 25%, 30%, 35%, 40%, 45%) by weight calcium phosphate material. Various embodiments of provided methods and compositions may provide compositions comprising between about 30% and about 50% (w/v) (e.g., 30% to 45%, 30% to 40%, 30% to 35%, 35% to 45%, 35% to 40%, 40% to 50%) calcium phosphate material.

In some embodiments, calcium phosphate material may be provided in a dry form, for example, a powder. In some embodiments, calcium phosphate material may be provided in a liquid suspension.

Formation of Provided Compositions

In some embodiments, provided methods comprise subjecting a composition comprising silk fibroin and at least one calcium phosphate material to crosslinking under conditions and for a period of time sufficient to convert the material from a first state that is substantially free of beta sheet character with no solid form structure to a second state having significant beta sheet character. In some embodiments, provided compositions are characterized in that an otherwise comparable composition lacking the calcium phosphate material and comparably exposed to crosslinking under the conditions and for the period of time does not produce a material with such beta sheet character and with such stiffness, toughness, and mechanical rigidity. In some embodiments, crosslinking is enzymatic crosslinking. In some embodiments, crosslinking is not enzymatic crosslinking.

Provided methods may produce compositions with varying degrees of solid content. In some embodiments, provided compositions comprise between 0.1% and 60% solids content (e.g., 0.1% to 50%, 0.1% to 40%, 0.1% to 30%, 0.1% to 20%, 0.1% to 10%, 1% to 60%, 1% to 50%, 1% to 40%, 1% to 30%, 1% to 20%, 1% to 10%). In some embodiments, the solids content of provided compositions comprises silk fibroin and at least one calcium phosphate material. In some embodiments, provided methods and compositions provide compositions wherein at least 80% (e.g., at least 85%, 90%, 95%) of the solids content comprises inorganic material (e.g., at least one calcium phosphate material).

Crosslinking

In some embodiments, provided compositions are formed, in whole or in part, through crosslinking of amino acid residues within silk protein. In some embodiments, introduction of crosslinks is via enzymatic crosslinking. For example, in some embodiments, provided methods comprise introduction of crosslinks as follows: contacting a silk solution with an enzyme (e.g., an oxidative enzyme) to form a silk-enzyme solution, associating the silk-enzyme solution with at least one calcium phosphate material to form a silk-calcium phosphate material mixture, and inducing crosslinking of the silk protein. In some embodiments, the inducing step includes associating the silk-calcium phosphate material mixture with a substrate to induce crosslinking. In some embodiments, provided methods employ a peroxidase enzyme (e.g., horseradish peroxidase) and a substrate (e.g., hydrogen peroxide) to enzymatically crosslink silk fibroin. In some embodiments, a silk solution may be associated with an enzyme before mixing with the calcium phosphate material (e.g., hydroxyapatite). In some embodiments, a silk solution may be associated with an enzyme substantially at the same time as with a calcium phosphate material.

Without wishing to be bound by a particular theory, it is possible that an enzyme (e.g., peroxidase enzyme) and substrate (e.g., hydrogen peroxide) may be used to enzymatically crosslink the tyrosine side chains that are found in native silk fibroin. According to various embodiments, the rate of crosslinking and/or kinetic properties of provided methods may be tunable or controlled, for example, depending on concentrations of silk, enzyme (e.g., HRP), and/or substrate for the enzyme (e.g., $H_2O_2$). In some embodiments, the kinetics of gelation may be controlled by adjusting factors other than silk concentration, including boil time, ratio of silk to calcium phosphate material, volume of the reaction, ratio of enzyme to substrate, and ratio of enzyme to silk.

According to various embodiments, crosslinking may be via an enzymatic mechanism. As discussed herein, any of a variety of enzymes may be used in accordance with various embodiments. In some embodiments, any oxidative crosslinking enzyme that allows for cross-linking of silk fibroin may be used. Examples of enzymes that may be used in accordance with various embodiments include, but are not limited to, lignin peroxidases (e.g., horseradish peroxidase, glutathione peroxidase, thyroid peroxidase, haloperoxidase, myeloperoxidase, animal-dependent peroxidase, vanadium bromoperoxidase, and/or lactoperoxidase), laccases, tyrosinases, oxidases, and oxidoreductases.

For embodiments including the use of enzymatic cross-linking, it is contemplated that at least one appropriate enzyme substrate is also used. In some embodiments, a crosslinking reaction is induced by an enzyme substrate. In some embodiments an enzyme substrate is a peroxide. In some embodiments, a peroxide is hydrogen peroxide, barium peroxide, calcium peroxide, sodium peroxide, organic peroxides or combinations thereof.

According to various embodiments, the ratio of enzyme to silk fibroin solution may vary in an application-appropriate manner. In some embodiments, the ratio of enzyme to silk fibroin solution is between 30 U/ml and 1,000 U/ml (e.g., 30 U/ml to 500 U/ml, 30 U/ml to 400 U/ml, 30 U/ml to 300 U/ml, 30 U/ml to 200 U/ml, 30 U/ml to 100 U/ml). In some embodiments, the ratio of enzyme to silk fibroin solution is at least 30 U/ml (e.g, at least 35 U/ml, 40 U/ml, 50 U/ml, 60 U/ml, 70 U/ml, 80 U/ml, 90 U/ml, 100 U/ml, 200 U/ml, 300 U/ml, or 500 U/ml). In some embodiments, the ratio of enzyme to silk fibroin solution is at most 1,000 U/ml (e.g., at most 900 U/ml, 800 U/ml, 700 U/ml, 600 U/ml, 500 U/ml, 400 U/ml, 300 U/ml, 200 U/ml, 100 U/ml). Without wishing to be held to a particular theory, it is possible that the ratio of enzyme to silk can affect the overall stiffness of some provided embodiments (e.g., the higher the ratio of enzyme to silk, the lower the stiffness of the composition).

In some embodiments, calcium phosphate material and silk-enzyme solution may be associated at any of a variety of ratios. In some embodiments, calcium phosphate material and silk-enzyme solution are associated at a ratio between 0.5 and 0.8 (e.g., 0.5 and 0.75, 0.5 and 0.7, 0.6 and 0.7). In some embodiments, the ratio of calcium phosphate material to silk solution is approximately 0.67 (±0.05).

By way of non-limiting example, in some embodiments, provided compositions may be formed using horseradish peroxidase as an enzyme and hydrogen peroxide as a substrate. In some such embodiments, the ratio of HRP to $H_2O_2$ is at least 750,000 units of active enzyme to mass of $H_2O_2$ in grams. In some embodiments, the volume of enzyme and volume of enzyme substrate are provided in a specific ratio or range of ratios, for example, a ratio of between 0.7 and 0.8 HRP:$H_2O_2$.

In some embodiments, cross-linking may be achieved using non-enzymatic methods. In some embodiments, non-enzymatic methods of achieving cross-linking include, but are not limited to dehydration (e.g., through exposure to alcohol treatment and/or nitrogen gas), mechanical force (e.g., shear stress), generation of radicals using, for example, UV light, and/or thermodynamic treatments.

Among the advantages provided by various embodiments, in some embodiments, provided methods allow for the formation of durable, flexible porous compositions. It is thought that traditional hydrogels form through physical entanglements and hydrogen bonding between hydrophobic domains, resulting in, among other things, β-sheet formation. β-sheet crystals have been shown to provide structure, strength, and long term stability of hydrogels. However, β-sheet crystals also typically display brittle behavior, as the crystals prevent long range displacements. While biomaterials formed from traditional hydrogels using β-sheet crystals and hydrogen bonding between hydrophobic domains provide surface seeding of cells, such hydrogels often require toxic crosslinking agents and solvents to support cell growth after proper curing and removal or inactivation of the deleterious substances. In contrast provided methods and compositions avoid many of these undesirable requirements and properties.

According to various embodiments, provided compositions may exhibit significant/substantial beta sheet character. In some embodiments, significant beta sheet character may be detected and/or characterized through the use of Fourier transform infrared spectroscopy (FTIR). In some embodiments, beta sheet character is detected through the generation of a peak at about 1625 $cm^{-1}$ using FTIR. In some embodiments, "significant beta sheet character" may be defined as at least a 50% difference in FTIP signal at 1625 $cm^{-1}$ between the first state and second state. In some embodiments, significant beta sheet character means more than 70%, 80%, 90%, or 95% of the silk exhibits beta sheet structure.

In some embodiments, provided methods allow for the production of strong yet flexible silk ceramic compositions (e.g., foams) with lower water content compared to hydrogels, including silk hydrogels. Due in part to the low water content of provided compositions, some embodiments, may be better classified as silk ceramic foams than as silk hydrogels. In some embodiments, provided compositions comprise 55% or less water content by weight. This is in contrast to a typical hydrogel, which comprises greater than 90% water content by weight and, in many cases, greater than 95%.

In some embodiments, provided compositions are biocompatible. For example, in some embodiments, such compositions (e.g., foams) have low to substantially no measurable cytotoxicity and/or do not appear to have any adverse or negative effects on the cells. In some embodiments, provided compositions are capable of supporting cellular proliferation and/or metabolism for at least one day (e.g., two days, three days, four days, five days, six days). In some embodiments, provided compositions are capable of supporting cellular proliferation and/or metabolism for at least one week (e.g., two weeks, three weeks, four weeks). In some embodiments, provided compositions are capable of supporting cellular proliferation and/or metabolism for at least one month (e.g., two months, three months, six months, twelve months).

According to various embodiments, addition of a substrate to a provided material will allow a cross-linking or other reaction to occur and "set" the composition (i.e., convert the material from a first state into a second state). In some embodiments, the time required for a provided composition to convert into a second state may vary in an application-appropriate manner. For example, in some embodiments, provided compositions (e.g., silk ceramic foams) convert to a second state in a period of time between 10 seconds and 10 minutes, inclusive (e.g., 30 seconds to 10 minutes, 1 minute to 10 minutes, 1 minute to 9 minutes, 1 minute to 8 minutes, 1 minute to 7 minutes, 1 minute to 6 minutes, 1 minute to 5 minutes, 1 minute to 4 minutes, 1 minute to 3 minutes, 1 minute to 2 minutes). In some embodiments, a provided material achieves a second state in at least 10 seconds (e.g., at least 20, 30, 40, 50, 60, 120, 180, 240, or 300 seconds). In some embodiments, a provided material achieves a second state in at most 10 minutes (e.g., at most 9, 8, 7, 6, 5, 4, 3, or 2 minutes).

According to various embodiments, provided compositions may form at temperatures at or above room temperature. In some embodiments, provided compositions form at 37° C. or higher. In some embodiments, increasing temperature may be used to accelerate the speed of the reaction to induce faster formation of provided compositions.

In some embodiments, provided compositions may have a very low inherent porosity. In some embodiments, one or more porogens may be used to increase the porosity of a particular composition prior to setting. In some such embodiments, after setting, the one or more porogens may be leached out of the composition (e.g., foam) to leave behind pores. According to various embodiments, any of a variety of porogens may be used. In some embodiments, a porogen may be or comprise particles (e.g., sodium chloride crystals or sucrose crystals), bubbles, polymeric porogens (such as polyethylene glycol, styrene, or polyvinyl), or any other porogen known in the art. In some embodiments, pores may be formed in provided compositions to facilitate, inter alia, the delivery of cells and/or drugs to one or more specific sites within a subject's body.

Additives

In some embodiments, provided compositions (e.g., foams) may further comprise one or more (e.g., one, two, three, four, five or more) additives. In some embodiments, an additive is or comprises an agent and/or functional moiety. Without wishing to be bound by a particular theory, in some embodiments, an additive may provide one or more desirable properties (e.g., strength, flexibility, ease of processing and handling, biocompatibility, bioresorbability, surface morphology, release rates and/or kinetics) to a particular provided composition and/or additive present in the composition. In some embodiments, an additive may be covalently or non-covalently linked with silk fibroin and/or may be integrated homogenously or heterogeneously within a provided silk composition.

In some embodiments, the properties of some provided compositions are tunable to use in specific cells and/or tissues. In some embodiments, provided compositions may be functionalized in order to, inter alia, support needs of cell engineering or tissue remodeling. In some embodiments, channels may be introduced (e.g., molded) into provided compositions to support cell infiltration for soft tissue repair and replacement by enhancing diffusion of oxygen and nutrients and promoting vascularization in critically sized defects. In some embodiments, provided compositions may be configured to control release of drugs and other therapeutic agents dispersed therein.

According to various embodiments, provided compositions may comprise any of a variety of amounts of additives. In some embodiments, provided compositions comprise a total amount of additives between about 0.01 wt % to about 99 wt %, from about 0.01 wt % to about 70 wt %, from about 5 wt % to about 60 wt %, from about 10 wt % to about 50 wt %, from about 15 wt % to about 45 wt %, or from about 20 wt % to about 40 wt %, of the total silk composition. In some embodiments, ratio of silk fibroin to additive in a provided composition ranges from about 1000:1 (w/w) to about 1:1000 (w/w), from about 500:1 (w/w) to about 1:500 (w/w), from about 250:1 (w/w) to about 1:250 (w/w), from about 200:1 (w/w) to about 1:200 (w/w), from about 25:1 (w/w) to about 1:25 (w/w), from about 20:1 (w/w) to about 1:20 (w/w), from about 10:1 (w/w) to about 1:10 (w/w), or from about 5:1 (w/w) to about 1:5 (w/w). In some embodiments, provided compositions do not include any additives.

In some embodiments, an additive may be or comprise one or more therapeutic agents. In some embodiments, a therapeutic agent is or comprises a small molecule and/or organic compound with pharmaceutical activity. In some embodiments, a therapeutic agent is or comprises a clinically used drug (e.g., an FDA-approved drug). In some embodiments, a therapeutic agent is or comprises one or more cells, proteins, peptides, nucleic acid analogues, nucleotides, oligonucleotides, nucleic acids (DNA, RNA, siRNA), peptide nucleic acids, aptamers, antibodies or fragments or portions thereof, anesthetic, anticoagulant, anticancer agent, inhibitor of an enzyme, steroidal agent, anti-inflammatory agent, anti-neoplastic agent, antigen, vaccine, antibody, decongestant, antihypertensive, sedative, birth control agent, progestational agent, anti-cholinergic, analgesic, anti-depressant, anti-psychotic, β-adrenergic blocking agent, diuretic, cardiovascular active agent, vasoactive agent, anti-glaucoma agent, neuroprotectant, angiogenesis inhibitor, hormones, hormone antagonists, growth factors or recombinant growth factors and fragments and variants thereof, cytokines, enzymes, antibiotics or antimicrobial compounds, antifungals, antivirals, toxins, prodrugs, chemotherapeutic agents, small molecules, drugs (e.g., drugs, dyes, amino acids, vitamins, antioxidants), pharmacologic agents, and combinations thereof.

In some embodiments, an additive may be or comprise one or more antibiotics. Exemplary antibiotics suitable for use in some embodiments include, but are not limited to, aminoglycosides (e.g., neomycin), ansamycins, carbacephem, carbapenems, cephalosporins (e.g., cefazolin, cefaclor, cefditoren, cefditoren, ceftobiprole), glycopeptides (e.g., vancomycin), macrolides (e.g., erythromycin, azithromycin), monobactams, penicillins (e.g., amoxicillin, ampicillin, cloxacillin, dicloxacillin, flucloxacillin), polypeptides (e.g., bacitracin, polymyxin B), quinolones (e.g., ciprofloxacin, enoxacin, gatifloxacin, ofloxacin, etc.), sulfonamides (e.g., sulfasalazine, trimethoprim, trimethoprim-sulfamethoxazole (co-trimoxazole)), tetracyclines (e.g., doxycyline, minocycline, tetracycline, etc.), chloramphenicol, lincomycin, clindamycin, ethambutol, mupirocin, metronidazole, pyrazinamide, thiamphenicol, rifampicin, thiamphenicl, dapsone, clofazimine, quinupristin, metronidazole, linezolid, isoniazid, fosfomycin, fusidic acid, β-lactam antibiotics, rifamycins, novobiocin, fusidate sodium, capreomycin, colistimethate, gramicidin, doxycycline, erythromycin, nalidixic acid, and vancomycin. For example, β-lactam antibiotics can be aziocillin, aztreonam, carbenicillin, cefoperazone, ceftriaxone, cephaloridine, cephalothin, moxalactam, piperacillin, ticarcillin and combination thereof.

In some embodiments, an additive may be or comprise an anti-inflammatory agent. Exemplary anti-inflammatory agents include, but are not limited to, corticosteroids (e.g., glucocorticoids), cycloplegics, non-steroidal anti-inflammatory drugs (NSAIDs), immune selective anti-inflammatory derivatives (ImSAIDs), and any combination thereof. Exemplary NSAIDs include, but not limited to, celecoxib (Celebrex®); rofecoxib (Vioxx®), etoricoxib (Arcoxia®), meloxicam (Mobic®), valdecoxib, diclofenac (Voltaren®, Cataflam®), etodolac (Lodine®), sulindac (Clinori®), aspirin, alclofenac, fenclofenac, diflunisal (Dolobid®), benorylate, fosfosal, salicylic acid including acetylsalicylic acid, sodium acetylsalicylic acid, calcium acetylsalicylic acid, and sodium salicylate; ibuprofen (Motrin), ketoprofen, carprofen, fenbufen, flurbiprofen, oxaprozin, suprofen, triaprofenic acid, fenoprofen, indoprofen, piroprofen, flufenamic, mefenamic, meclofenamic, niflumic, salsalate, rolmerin, fentiazac, tilomisole, oxyphenbutazone, phenylbutazone, apazone, feprazone, sudoxicam, isoxicam, tenoxicam, piroxicam (Feldene®), indomethacin (Indocin®), nabumetone (Relafen®), naproxen (Naprosyn®), tolmetin, lumiracoxib, parecoxib, licofelone (ML3000), including pharmaceutically acceptable salts, isomers, enantiomers, derivatives, prodrugs, crystal polymorphs, amorphous modifications, co-crystals and combinations thereof.

In some embodiments, an additive may be or comprise an antibody. In some embodiments, an antibody may be or comprise abciximab, adalimumab, alemtuzumab, basiliximab, bevacizumab, cetuximab, certolizumab pegol, daclizumab, eculizumab, efalizumab, gemtuzumab, ibritumomab tiuxetan, infliximab, muromonab-CD3, natalizumab, ofatumumab omalizumab, palivizumab, panitumumab, ranibizumab, rituximab, tositumomab, trastuzumab, altumomab pentetate, arcitumomab, atlizumab, bectumomab, belimumab, besilesomab, biciromab, canakinumab, capromab pendetide, catumaxomab, denosumab, edrecolomab, efungumab, ertumaxomab, etaracizumab, fanolesomab, fontolizumab, gemtuzumab ozogamicin, golimumab, igovomab, imciromab, labetuzumab, mepolizumab, motavizumab, nimotuzumab, nofetumomab merpentan, oregovomab, pemtumomab, pertuzumab, rovelizumab, ruplizumab, sulesomab, tacatuzumab tetraxetan, tefibazumab, tocilizumab, ustekinumab, visilizumab, votumumab, zalutumumab, and zanolimumab.

In some embodiments, an additive may be or comprise a polypeptide (e.g., protein), including but are not limited to: one or more antigens, cytokines, hormones, chemokines, enzymes, and any combination thereof as an agent and/or functional group. Exemplary enzymes suitable for use herein include, but are not limited to, lipase, amylose, organophosphate dehydrogenase, ligases, restriction endonucleases, ribonucleases, DNA polymerases, and the like.

Additives—Growth Factors

In some embodiments, an additive may be or comprise one or more growth factors. In some embodiments, a provided composition may comprise multiple growth factors. Exemplary growth factors compatible with some embodiments, include, but are not limited to, adrenomedullin, angiopoietin, autocrine motility factor, brain-derived neurotrophic factor, bone morphogenetic protein, colony-stimulating factors, connective tissue growth factor, epidermal growth factor, erythropoietin, fibroblast growth factor, glial cell line-derived neurotrophic factor, granulocyte colony stimulating factor, granulocyte macrophage colony stimulating factor, growth differentiation factor-9, hepatocyte growth factor, hepatoma-derived growth factor, insulin-like growth factor, interleukins, keratinocyte growth factor, myostatin, nerve growth factor, neurotrophins, platelet-derived growth factor, placenta growth factor, thrombopoietin, transforming growth factor alpha, transforming growth factor beta, tumor necrosis factor-alpha, vascular endothelial growth factor and combinations thereof.

Mechanical Properties of Provided Compositions

As discussed herein, in some embodiments, compositions of the present invention may be or comprise flexible ceramic compositions formed, in whole or in part, through silk polymeric crosslinking. One of the many advantages provided by various embodiments is that provided compositions avoid the traditional brittleness associated with standard ceramics. In some embodiments, provided compositions are comprised of a high proportion of ceramic material to silk binder. Without wishing to be held to a particular theory, it is possible that the silk binder imparts flexibility and a unique toughness to the ceramic structure and is formed covalently through crosslinking of, for example, tyrosine residues within silk protein. It is contemplated that crosslinking of amino acid residues within silk leads to an increase in beta sheet character and an enhancement of the overall order of the protein structure. In some embodiments, the silk ceramic foam comprises substantial beta sheet formation.

Various embodiments may exhibit any of a range of Young's modulus (also known as tensile modulus or elastic modulus). According to various embodiments, provided compositions may have a Young's modulus of between 2-4 MPa (e.g., 2-3.5 MPa, 2-3.5 MPa, 2.5-4 MPa, 2.5-3.5 MPa), for example.

Various embodiments, may also exhibit any of a range of compressive strengths. For example, in some embodiments, provided compositions may be characterized as having a compressive strength between 0.1-2 MPa (e.g., 0.1-1.5 MPa, 0.1-1 MPa, 0.5-2 MPa, 0.5-1.5 MPa).

According to certain embodiments, provided compositions may exhibit varying degrees of compressive toughness. For example, in some embodiments, provided compositions are characterized as having a compressive toughness between 1-20 kJ m$^{-3}$.

According to certain embodiments, provided compositions may exhibit varying degrees of compressive elastic modulus. In some embodiments, provided compositions are characterized as having a compressive elastic modulus between 1-5 MPa at 5% strain (e.g., 1-4 MPA, 1-3 MPa, 1-2 MPa, 2-5 MPa, 2-4 MPa, 3-4 MPa).

As described herein, various mechanical and other properties of provided compositions may be tuned/modified by varying one or more parameters of provided methods. In some embodiments, for example, stiffness and/or mechanical strength of provided compositions may be tuned based on the powder to liquid ratio of the calcium phosphate material-silk paste. In some embodiments, provided silk ceramic compositions are flexible yet firm enough to serve as a replacement for osseous tissue.

Exemplary Uses

Provided methods and compositions may be used in a wide range of processes and for any of a variety of uses. In some embodiments, provided compositions (e.g., foams) are useful in one or more medical procedures. By way of non-limiting example, in some embodiments, provided compositions may be used to form all or part of certain osteotomy wedges used in surgeries to repair or correct bone malformations. Alternatively or additionally, provided compositions may be or comprise a medical implant. In some embodiments, provided compositions set rapidly and are injectable, allowing one to injection mold implantable parts to repair or replace bone and osseous tissue.

In some embodiments, provided compositions may also be used as injectable, flexible foams in osteochondral applications for cartilage or trabecular bone repair or as bone augmentation matrices for joint repair. In some embodiments, provided compositions have dental applications as osteoconductive packing material for gum and dental repair a swell as drug/antibiotic release depots. In some embodiments, provided compositions may be injection molded to form rapidly setting, complex geometrical parts for implantation.

In some embodiments, provided compositions may be delivered to a site of medical treatment through a self-mixing syringe. In some embodiments, a syringe may keep components separate prior to use, mixing the components as they are injected. Alternatively, according to various embodiments, the setting time of the mixture can be tailored to provide a clinician enough time to first mix the components and then apply the syringe to the site of treatment.

In other embodiments, silk used in provided compositions may be in solution or, alternatively, a solid state for better stability and easier storage. In some embodiments, silk provided as a soluble dry-silk powder can be re-dissolved in aqueous media either prior to or during crosslinking. In some embodiments, silk and calcium phosphate material (e.g., hydroxyapatite) powders can be mixed in a desired ratio and combined with water to form a paste prior to exposure to crosslinking processes and/or reagents. Furthermore, in some embodiments, aqueous media could also contain biomolecules and/or bioactive components that, once mixed with the calcium phosphate material/silk solution and cross-linked, would be trapped within the organic-inorganic network and would serve as a drug depot to release as the material degrades.

In some embodiments, the provided compositions (e.g., foams) may be suitable for supporting cell growth and/or maintenance. In some embodiments, provided compositions may further comprise a cell. In some embodiments, a cell may be or comprise a bone cell (e.g., osteoblasts, osteoclasts), stem cell (e.g., a human mesenchymal stem cell), and/or chondrocytes. In some embodiments, provided compositions are capable of supporting cellular proliferation and/or metabolism for at least one day. In some embodiments, provided compositions are capable of supporting cellular proliferation and/or metabolism for at least one week. In some embodiments, provided compositions are capable of supporting cellular proliferation and/or metabolism for at least ten days. In some embodiments, provided compositions are capable of supporting cellular proliferation and/or metabolism for at least one month. In some embodiments, provided compositions are capable of supporting cellular proliferation and/or metabolism for at least one year.

Routes of Administration

Foams of the present invention may be administered by any appropriate route which results in effective treatment in the subject, i.e. administration results in delivery to a desired location in the subject where at least a portion of the pharmaceutically active agent is delivered. Exemplary modes of administration include, but are not limited to, topical, implant, injection, infusion, spray, instillation, implantation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion.

Example

The following example illustrates some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

Unless otherwise specified, the materials and methods used in this Example were as follows:

The materials used in this Example were: aqueous silk solution (6% wt/volume after either a 30 or 60 minute boil time, as described below); horseradish peroxidase (HRP) enzyme (5,000 U/ml); hydrogen peroxide (0.5% wt/vol $H_2O_2$ stock solution); hydroxyapatite (HA) powder (Fisher Scientific catalog # AC37126-0010); and PDMS or Dragon Skin mold for scaffold casting.

Preparation of Aqueous Silk Solution:

Silk solutions were prepared using the previously established procedure (D. N. Rockwood, et. al., 6 Nature protocols 1612 (2011) which is hereby incorporated by reference in it entirety. Briefly, 5 grams of *B. mori* silkworm cocoons were immersed in 1 L of boiling 0.02 M $Na_2CO_3$ solution for 30 or 60 minutes, subsequently referred to as 30 mb and 60 mb respectively, to, inter alia, remove the sericin protein. Degummed fibers were collected and rinsed with distilled water three times, then air-dried. The fibers were solubilized in 9.3 M LiBr (20% w/v) at 60° C. for 4 hours. A volume of 15 mL of this solution was then dialyzed against 1 L of distilled water (water changes after 1, 3, 6, 24, 36, and 48 hours) with a regenerated cellulose membrane (3500 MWCO, Slide-A-Lyzer, Pierce, Rockford, Ill.). The solubilized silk protein solution was then centrifuged twice (9700 RPM, 20 min., 4° C.) to remove insoluble particulates. Protein concentration was then determined by drying a known mass of the silk solution under a hood for 12 hours and assessing the mass of the remaining solids.

Methods for Preparation of HA-Silk Ceramic Foams:

FIG. 1 depicts the steps used in this Example to create exemplary provided compositions, here HA-silk foams. Briefly, a mixture of silk solution with HRP enzyme was created by adding 40 µL of HRP stock solution (10,000 U/mL) to 4 mL of silk solution, which was then mixed thoroughly (see FIG. 1A-1C). Note that, according to various embodiments, any HRP concentration may be used as long as the HRP/silk ratio is at or above 33 U/mL. Next, the silk-HRP solution was mixed with 2 grams of dry HA powder and the resultant mixture was stirred until a homogenous HA-silk-HRP paste was formed (FIG. 1D). In this Example, the HA powder was dissolved/dispersed in the silk solution first (to completely surround the HA particles with silk prior to addition of enzyme/peroxide). In some embodiments, additional water may be added as needed after this step to ensure formation of a homogenous paste. While not wishing to be held to a particular theory, it may be desirable that the HA is not dissolved/dispersed in water first and then combined with silk solution since this may prevent complete mixing of the HA with the silk, possibly at least in part due to the hydrophobic nature of the silk. Rather, it is possible that mixing the HRP enzyme into the silk solution prior to mixing the silk with the HA allows for better distribution of the HRP throughout the HA/silk paste; however, this is not required for scaffold formation and instead the HRP could be added directly to the HA/silk paste.

In this Example, a 6% wt/vol 30-minute boil silk solution was used to create the desired paste consistency at P/L 0.67. Using a higher concentration silk (generally above 8% wt/vol) may require the addition of more water to form the HA/silk paste due to poorer dispersion of HA in high concentration silk. The use of low molecular weight (low boil time) silk solution may also require addition of more water to form a paste for the same reason. HA/silk foams containing a lower concentration of HA may be made by addition of more silk material, however, this will alter the P/L as more silk solution is added (or as HA is removed from the standard 2 gram amount used in this Example). To avoid this problem, in some embodiments, silk material can be combined with the HA in the form of a soluble silk powder rather than as an aqueous solution. Thus, in some embodiments, the desired amount of silk and HA can be combined in solid state, and water can then be added to obtain the desired paste consistency prior to addition of HRP enzyme and hydrogen peroxide.

Next, 50 µL of the 0.5% $H_2O_2$ was added to the HA-silk-HRP paste and mixed vigorously (FIG. 1E). A 1:2 volumetric ratio of HRP enzyme (5,000 U/mL) to hydrogen peroxide (1% stock solution) was used in this Example rather than a 1:1 ratio of HRP (5,000 U/mL) to $H_2O_2$ (0.5% wt solution) because, according to various embodiments, it may be desirable to use a greater volume of a more dilute $H_2O_2$ stock solution since it permits better mixing and distribution of the peroxide throughout the HA-silk paste mixture.

Figure 3:
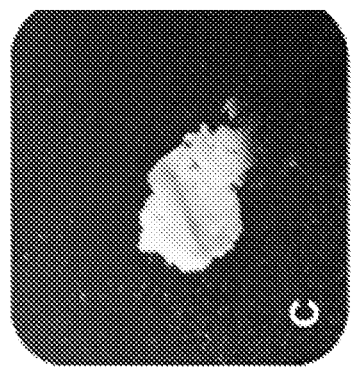
FIG. 3 shows exemplary photographs of compositions created according to methods previously known.
Figure 3:
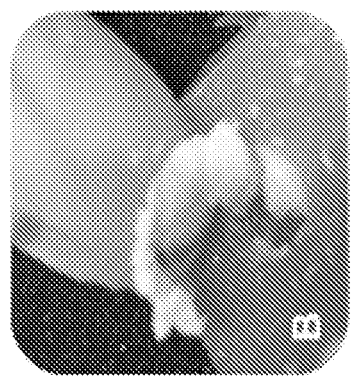
Figure 3:
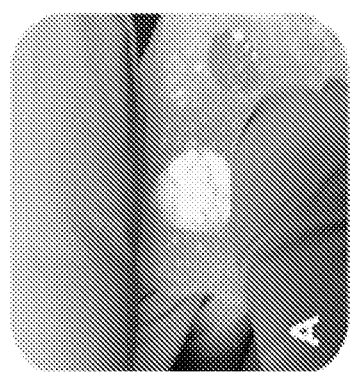

Depending on the HRP, $H_2O_2$, and silk ratios used to make particular HA-silk foam embodiments, the setting or hardening of the HA/silk composition may begin within as little as 10-15 seconds of adding the hydrogen peroxide initiator (as evidenced by a noticeable thickening and loss of paste consistency). Without wishing to be held to a particular theory, it is possible that complete setting of the HRP-ceramic foams will occur within a 3-5 minutes after hydrogen peroxide addition, and can be accelerated by placing the mold at 60° C. for 1-2 minutes. In some embodiments, as shown in this Example, both HRP (enzyme) and hydrogen peroxide (substrate) are required for formation of a provided composition (here a ceramic foam). Without these two components, the foams will not form properly as depicted in FIG. 3. In some embodiments, decreasing the HRP/silk (U/mL) ratio may help to increase the time constant of the setting reaction to allow more time for molding. In some embodiments, increasing the concentration of $H_2O_2$ used may also help to slow down the reaction and allow more time for molding prior to setting.

Figure 2:
FIG. 2 shows exemplary photographs of certain embodiments. Specifically.
Figure 2:
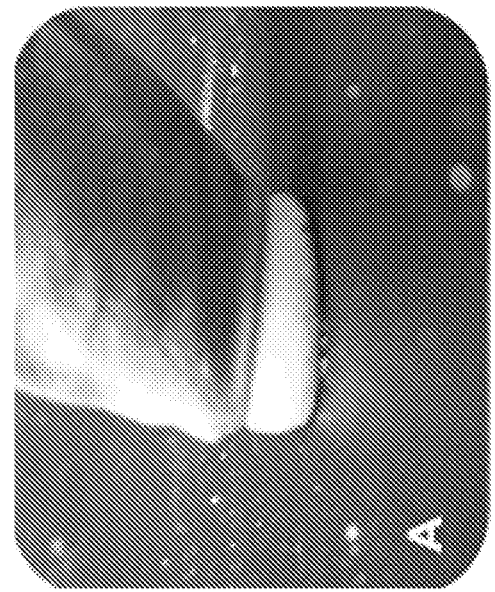

In this Example, after addition of $H_2O_2$, the paste was immediately placed in the PDMS or Dragon Skin mold by hand, and care was taken to ensure complete packing of the HA-silk material within the mold to remove air pockets (see FIG. 1F). The paste was left in the mold at room temperature for at least 5 minutes to set. After 5 minutes a room temperature, the HA-silk foams could be carefully peeled away from the PDMS mold (FIGS. 1G & 1H). Finished HA-silk scaffolds were stored in either distilled water or DMEM (1×) at room temperature or at 4° C. until use (FIG. 1I). Upon successful setting, the resulting firm and flexible HA-silk ceramic foams could be manipulated as shown in FIG. 2.

Structural Characterization:

In this Example, enzymatically crosslinked ceramic foam gel samples were evaluated using Fourier Transform Infrared, Attenuated Total Reflectance Spectroscopy (FTIR) in an attempt to determine foam conformation and structure. To perform FTIR, samples of foam and silk solution mixed with HRP were dried at room temperature in a fume hood for 12 hours. Spectra were then recorded from 600-4,000 $cm^{-1}$ using 32 co-added scans at a resolution of 4 $cm^{-1}$ and subjected to ATR correction using JASCO Spectra Analysis software.

Figure 4:
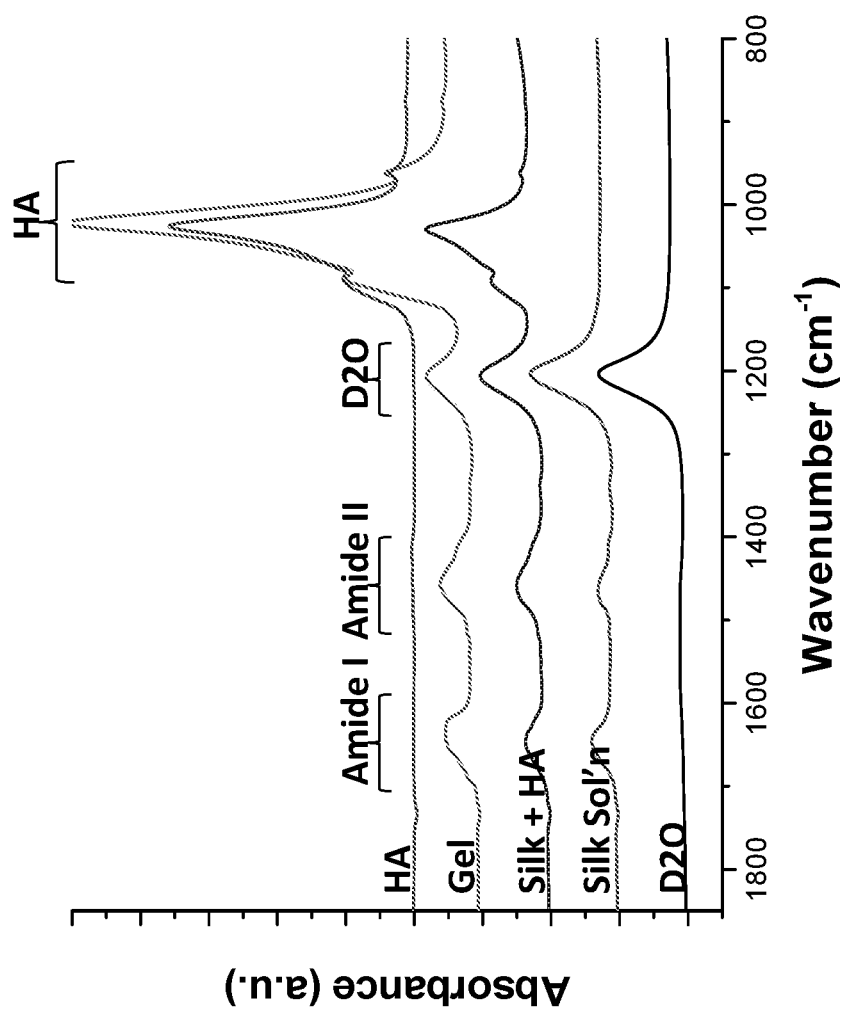
FIG. 4 depicts an exemplary Fourier Transform Infra-Red (FTIR) spectra of pertinent peaks of certain exemplary compositions as compared to hydroxyapatite (HA) alone, a gel, a silk solution alone, deuterium oxide ($D_2O$). Peaks corresponding to amide I, amide II, $D_2O$ and HA are labeled for the absorbance of HA, gel, silk and HA, silk solution and D2O. In this figure, the "gel" condition was a silk only hydrogel made by mixing the silk solution with HRP and peroxide without any CaP; the concentration of the silk used in the gel condition was 6% wt/v and the boil time was 60 min.
Figure 5:
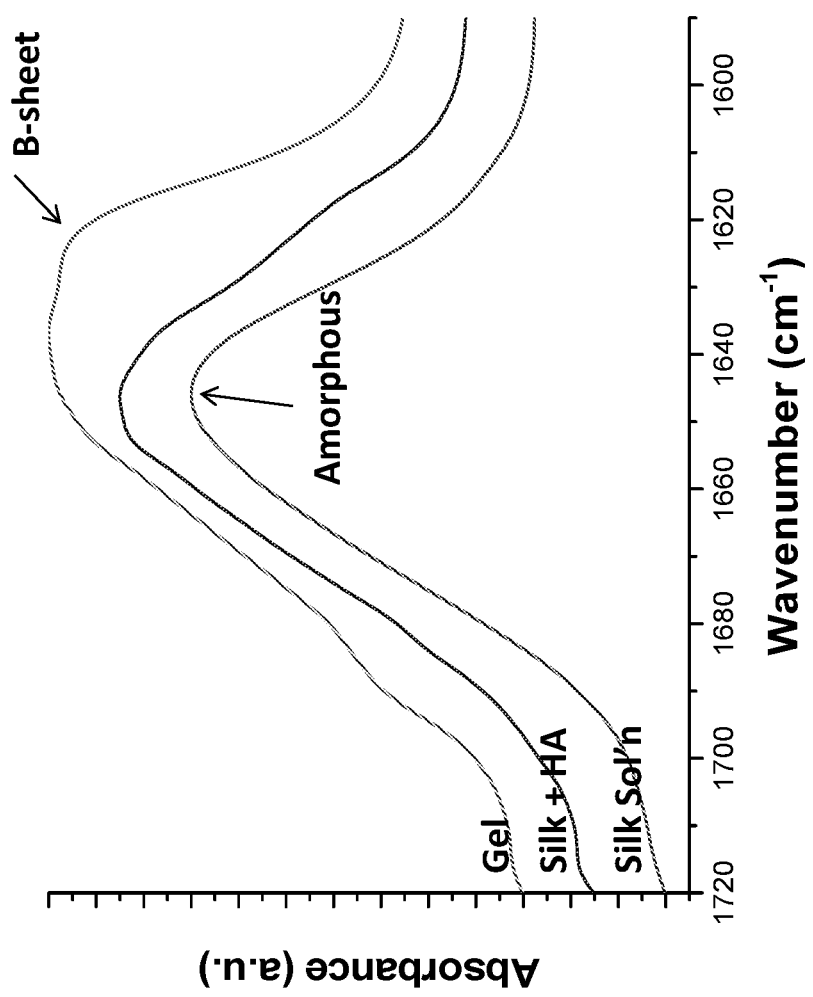
FIG. 5 depicts an exemplary Fourier Transform Infra-Red (FTIR) spectra of the Amide I region peak for a gel, silk and HA and silk solution. Note the shift in peak wavenumber from unreacted silk solution to silk and HA to gel. The Amide I region peak is amorphous for silk solution alone but becomes more ordered with beta sheet character as a gel forms. In this figure, the "gel" condition was a silk only hydrogel made by mixing the silk solution with HRP and peroxide without any CaP; the concentration of the silk used in the gel condition was 6% wt/v and the boil time was 60 min.

Silk solution, silk with hydroxyapatite (HA), hydroxyapatite alone, gel/foam alone and $D_2O$ were all analyzed by FTIR. FIG. 4 depicts the FTIR spectra of all relevant peaks for the various silk substances analyzed. Peaks consistent with Amide I region, Amide II region, $D_2O$, and HA are marked for each of the silk forms at their respective absorbance values. FIG. 5 depicts the FTIR spectra of the Amide I region for silk solution, silk with hydroxyapatite (HA), and gel alone. As shown in FIG. 5, the silk solution peak at 1640 cm$^{-1}$ corresponds to a more amorphous structure. Consequently, the 1620 cm$^{-1}$ peak for gel represents a significant increase in ordered beta sheet structure seen in the final ceramic foam. The FTIR spectra of a dried gel sample exhibits an amide I spectra characteristic of high beta sheet content, with a pronounced peak at 1620 cm$^{-1}$. This is in contrast to the silk and HRP solution that exhibits a broad peak centered on 1640 cm$^{-1}$, indicative of a primarily random coil, amorphous sample. This suggests that the tyrosine crosslinks align the fibroin molecules in a manner that localizes the domains involved in beta sheet formation, allowing the hydrogen bonding to occur without the need for additional treatments to induce crystallization.

Cyclic Compression Testing:

Unconfined compression tests were conducted to assess the mechanical properties of the HA-silk foams as well as recovery following cyclic compression. HA-silk foams (7 mm 0, 3 mm h) were prepared and equilibrated in PBS 1× for 12 hours prior to testing. The final diameter after equilibration was measured and used for compressive stress calculations. Samples were loaded in a TA instruments RSA3 dynamic mechanical analyzer between parallel steel plates in a PBS 1× immersion bath. All tests were conducted in PBS 1× at 25° C. The upper plate was lowered until a compressive force pre-load of −3 g was registered. Samples were subjected to 35% strain at a strain rate of 0.05 mm/second, and subsequently allowed to recover to determine hysteresis behavior. Fatigue stability of the foams was assessed by monitoring the dynamic modulus using frequency sweeps (0.1, 1, 10, 50 Hz) conducted at a strain of 0.5%.

Figure 6:
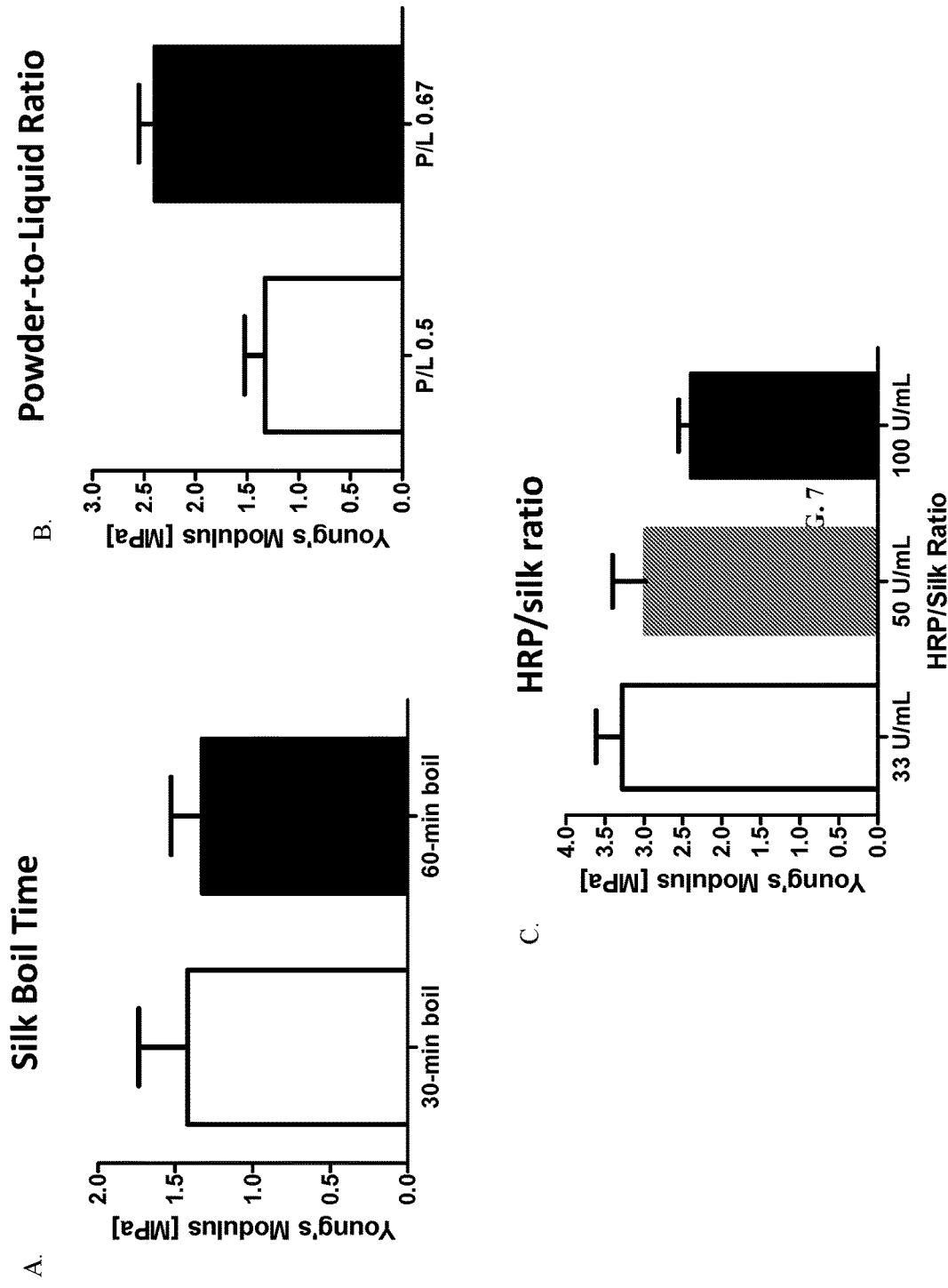
FIG. 6 depicts the effects of altering certain elements of provided methods on the compressive properties of certain exemplary provided compositions. HA-silk foam samples were subjected to 35% strain and equilibrated to determine the Young's modulus from the linear stress-strain region.

To illustrate certain exemplary effects of varying provided reaction conditions during the formation of provided foams, tests were performed to characterize certain mechanical properties, such as the Young's Modulus. As depicted in FIG. 6A, 30 minute and 60 minute boil times give similar Young's Moduli—between 1.0 and 2.0 MPa. FIG. 6B depicts the effect on silk ceramic foams by altering the powder-to-liquid (P/L) ratio. A powder-to-liquid (P/L) ratio of 0.5 leads to a Young's Modulus of approximately 1.25-1.5 MPa while a P/L of 0.67 leads to a Young's Modulus of approximately 2.25-2.5 MPa. A decrease in Young's Modulus is seen as the ratio of HRP to silk increases (see FIG. 6C).

Figure 7:
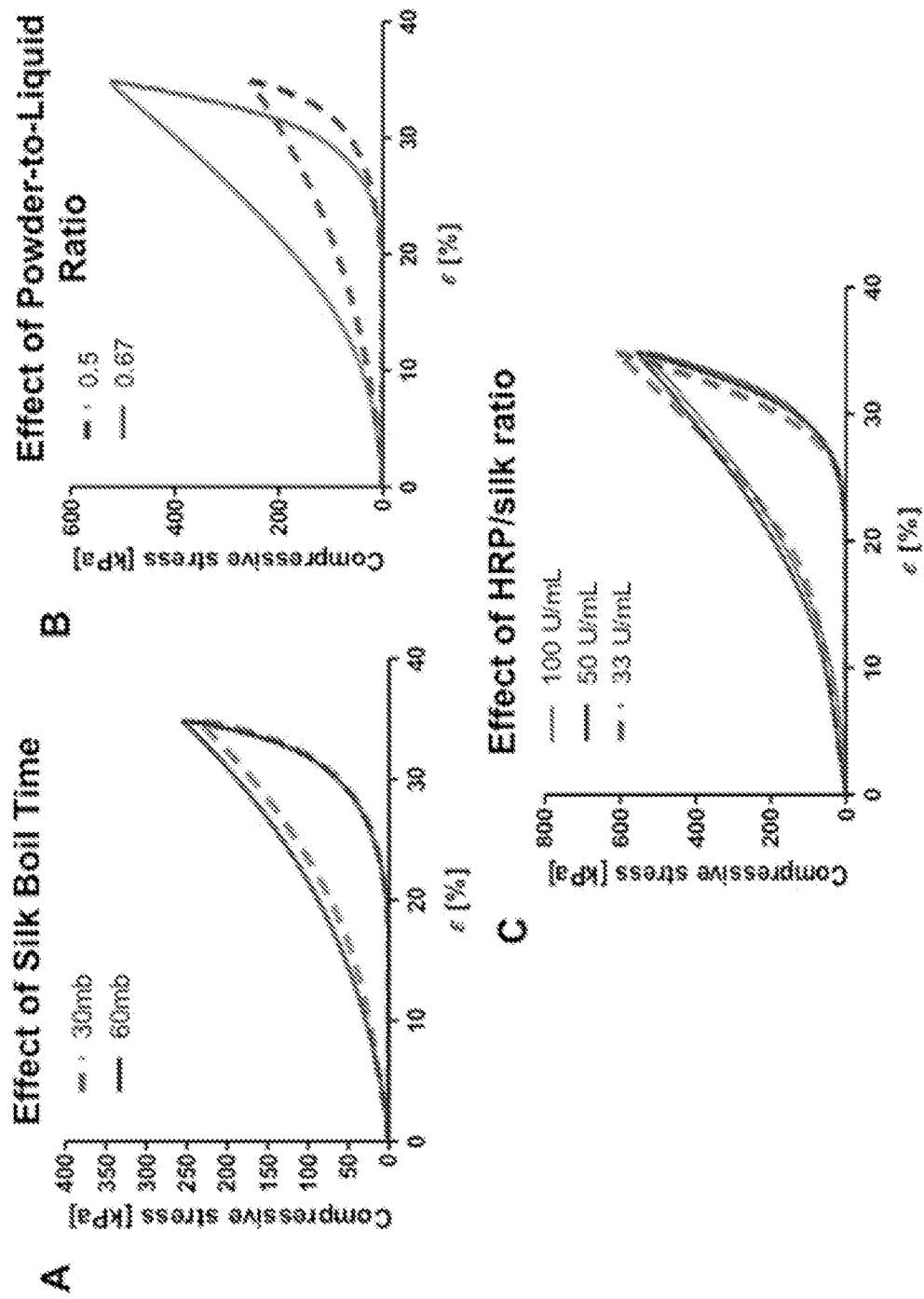
FIG. 7 depicts the effects of altering certain elements of provided methods on the compressive properties of certain exemplary provided compositions.

FIG. 7 depicts exemplary data examining the effects of altering reaction conditions on the elastic hysteresis of provided foams. As depicted in FIG. 7, provided silk foams, in some embodiments, experience recovery to 20% strain. In this Example, altering the boil times from 30 and 60 minutes did not appear to alter the response to compressive stress (see FIG. 7A). It also appeared that a change in HRP to silk ratio from 33 U/mL to 50 U/mL to 100 U/mL did not alter the compressive stress response (FIG. 7C). As seen in FIG. 7B, reducing the powder-to-liquid ratio from 0.67 to 0.5 appeared to cause a reduction in the compressive stress response of the foams in this Example.

Figure 8:
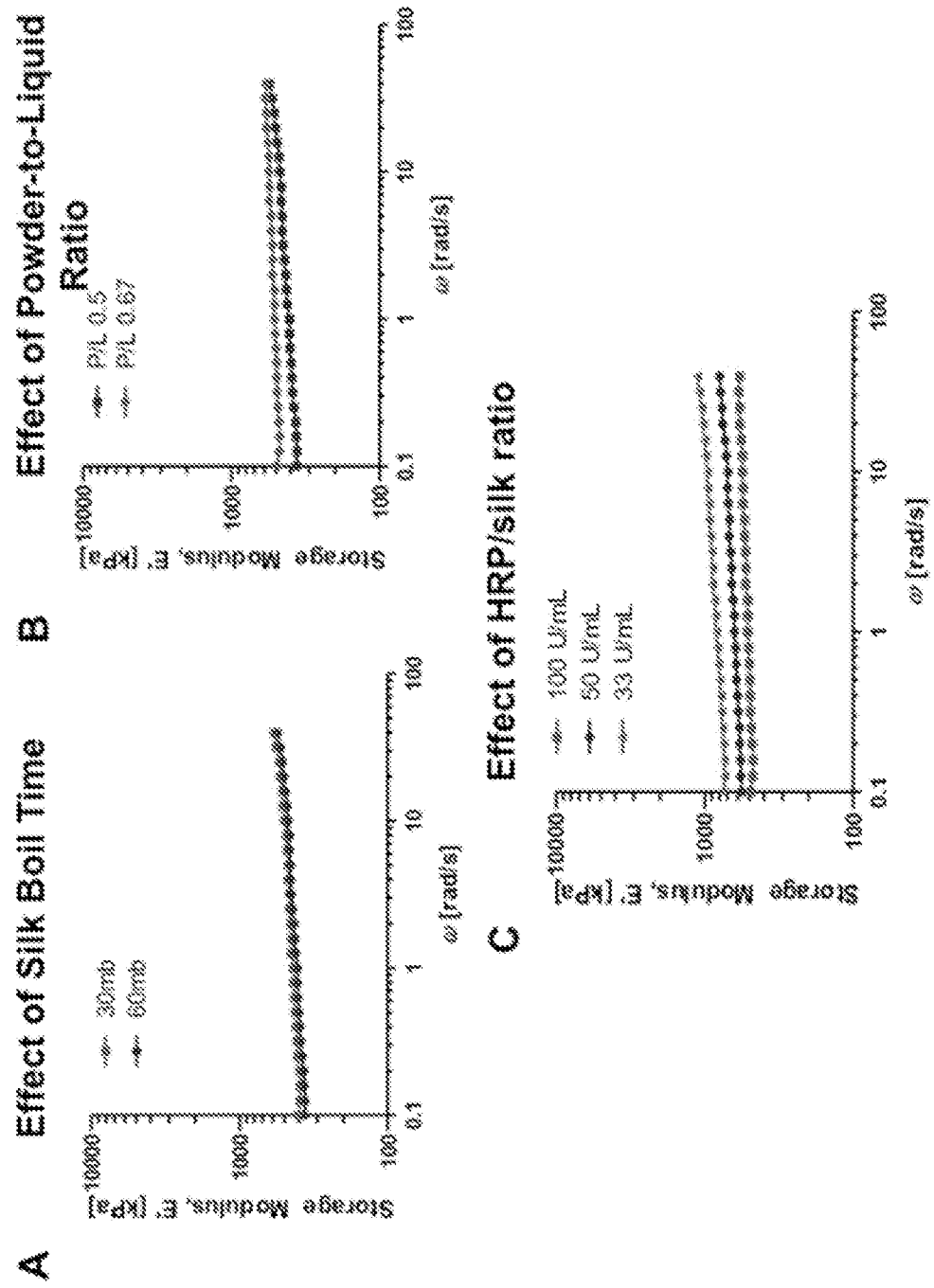
FIG. 8 depicts the effects of loading frequency on the storage modulus (E') of certain exemplary embodiments. Samples were tested using unconfined compression over a frequency range from 0.1 to 40 Hz. No significant frequency-dependent stiffening of the HA-silk foam embodiment was observed. Specifically.

Mechanical Properties of Ceramic Silk Foams:

The compressive properties of the enzymatically cross-linked silk foams produced as described in this Example were assessed using cyclic unconfined compression in a dynamic mechanical analyzer for each of the reaction conditions studied previously (boil time, powder-to-liquid ratio, and HRP/silk ratio). The strain responses under different reaction conditions are shown in FIG. 8A-C. All foams tested, regardless of the reaction conditions that generated them, gave similar storage moduli and were frequency independent.

Figure 9:
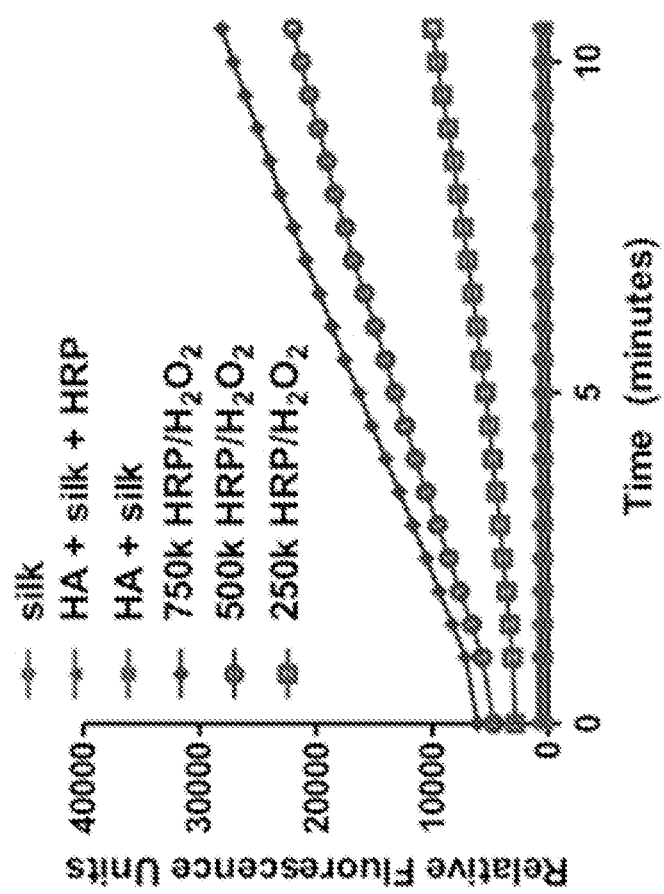
FIG. 9 depicts the effects of altering certain elements of provided methods on the formation kinetics of certain exemplary provided compositions. The rate of HA-silk foam formation was measured using fluorescence monitoring of dityrosine bond formation within a silk binder. The effect of peroxide concentration (HRP/peroxide ratio) on formation rate was assessed at ratios of 750,000 U HRP/g $H_2O_2$, 500,000 U HRP/g $H_2O_2$, and 250,000 HRP U/g $H_2O_2$ using 6% wt/v 60-minute boil silk with hydroxyapatite at a P/L ratio of 0.67. The rise in relative fluorescence units (RFU) is plotted versus time in minutes.
Figure 10:
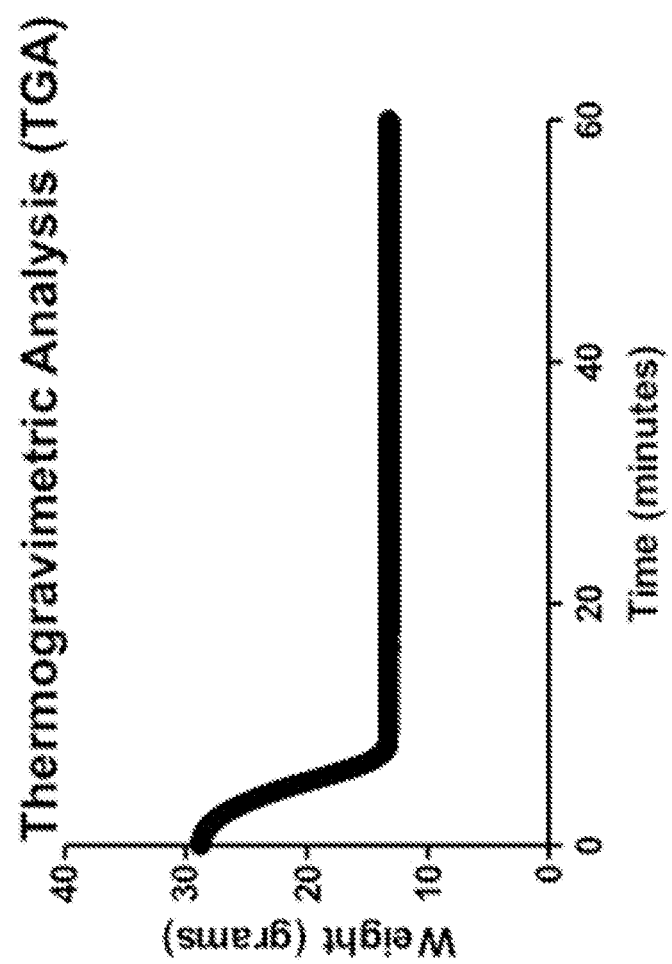
FIG. 10 depicts the thermogravimetric analysis (TGA) of certain exemplary embodiments. TGA was conducted on pre-hydrated HA-silk foams that were prepared using 30-minute boil, 6% wt/v silk and an HRP/$H_2O_2$ ratio of 500,000 U/g. TGA testing was conducted over a temperature range of 25° C. to 120° C. at a rate of 20° C./minute to assess water content. Water content of certain exemplary embodiments was determined to be 54.2% by mass.
Figure 11:
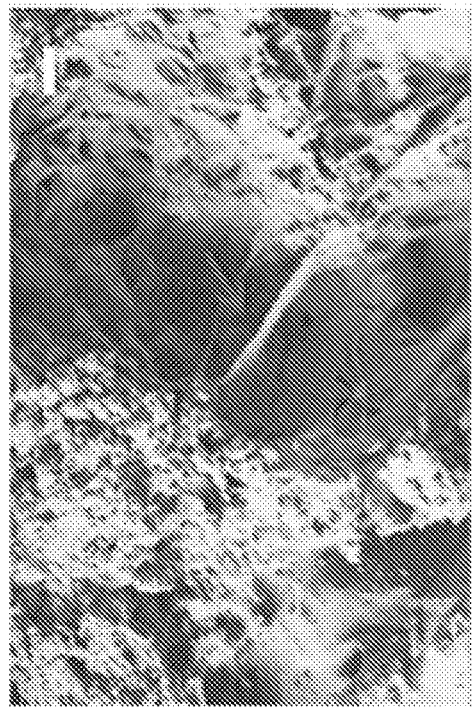
FIG. 11 shows exemplary photographs of the scaffold morphology of certain exemplary embodiments. HA-silk samples prepared using 30-minute boil, 6% wt/v silk and an HRP/$H_2O_2$ ratio of 500,000 U/g were freeze-dried, fractured, and sputter coated with gold. Scanning electron microscopy imaging of the exemplary embodiments was conducted at 5 kV. Scale bars are 20 μm. Red arrows indicate silk strands acting as a binder to reinforce the hydroxyapatite matrix.
Figure 11:
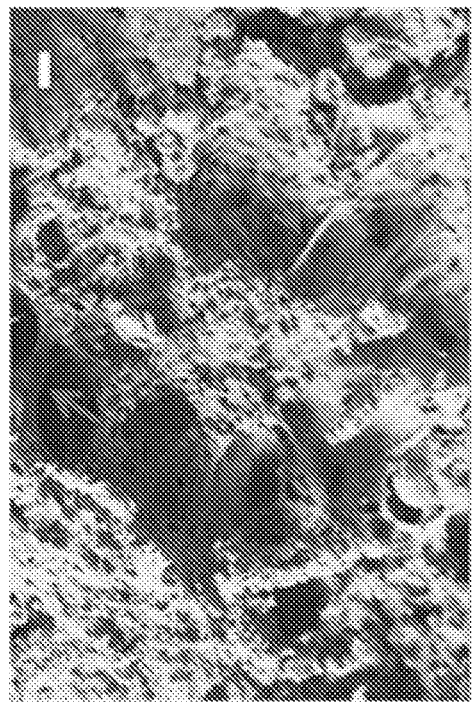
Figure 12:
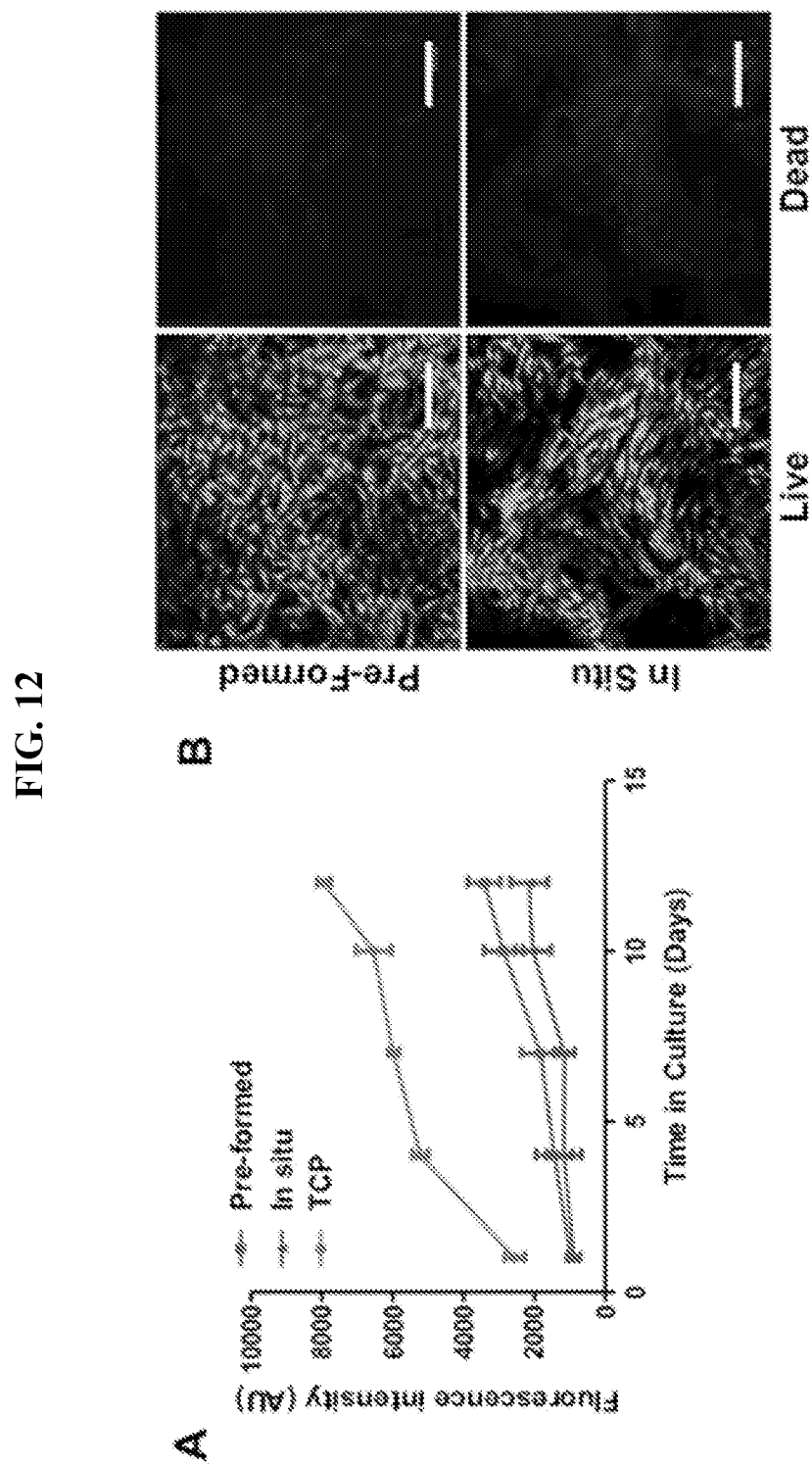
FIG. 12 depicts the response of bone marrow-derived human mesenchymal stem cells (hMSCs) to certain exemplary embodiments. Pre-formed and in situ formed HA-silk foams were surface seeded with 100,000 hMSCs per scaffold.

Formation Kinetics:

To assess setting kinetics, dityrosine formation during HA-silk foam formation was monitored by quantifying fluorescence using a plate reader with an excitation wavelength of 550 nm and an emission wavelength of 590 nm. FIG. 9 depicts an exemplary graph of the formation kinetics of silk foams of the present invention.

EQUIVALENTS

While the present invention has been described herein in conjunction with various embodiments and examples, it is not intended that the scope be limited to such embodiments or examples. On the contrary, the present invention encompasses various alternatives, modifications, and equivalents, as will be appreciated by those of skill in the art. Accordingly, the descriptions, methods and diagrams of should not be read as limited to the described order of elements unless stated to that effect.

What is claimed:

1. A method of producing a silk ceramic material, the method comprising steps of: subjecting a composition comprising:
   silk fibroin; and
   a calcium phosphate material;
   to enzymatic crosslinking under conditions and for a period of time sufficient to convert the material from a first state that is substantially free of beta sheet structure with no solid form structure to a second solidified state having more than 70% beta sheet structure.

2. The method of claim 1 wherein the silk fibroin is present in the composition at a weight percent within the range of about 0.1% to about 50%, inclusive.

3. The method of claim 1 wherein the calcium phosphate material is present in the composition at a weight percent within the range of about 30% to about 50%.

4. The method of claim 1, wherein the calcium phosphate material and silk fibroin are present in relative weight percent amounts within the range of 1:2 to 4:5.

5. The method of claim 1, wherein the silk fibroin has a molecular weight within the range of about 10 kDa to about 450 kDa.

6. The method of claim 1, wherein the composition is a solution.

7. The method of claim 1, wherein the composition is a paste.

8. The method of claim 1, wherein:
   the composition further comprises a crosslinking enzyme; and
   the step of subjecting comprises adding to the composition a substrate for the enzyme so that the enzyme introduces crosslinks into the composition.

9. The method of claim 8, wherein the crosslinks comprise crosslinks between silk fibroin tyrosine residues.

10. The method of claim 8, wherein the crosslinking enzyme is selected from a peroxidase, a lignin peroxidase, laccase, tyrosinase, an oxidase, and an oxidoreductase.

11. The method of claim 1, wherein the second state is characterized as having at least one of a compressive toughness of between 1-20 kJm$^3$, inclusive or a compressive elastic modulus between 1-5 MPa at 5% strain, inclusive.

12. The method of claim 1, further comprising a step of providing the composition by combining:
   a solution comprising the silk fibroin; and
   a powder comprising the calcium phosphate material.

13. The method of claim 12, wherein the solution is prepared by a process that includes boiling for a period of time within the range of 1 minute to 120 minutes, inclusive.

14. The method of claim 12, wherein the boiling is performed under conditions and for a period of time so that the silk fibroin has a molecular weight within the range of 300 kDa to 450 kDa.

15. The method of claim 12, wherein the boiling is performed under conditions and for a period of time so that the silk fibroin has a molecular weight within the range of 10 kDa to 300 kDa.

16. The method of claim 12, wherein the step of providing the composition comprises combining the powder and the solution in a relative proportion within the range of 0.5 to 0.8.

* * * * *